United States Patent [19]

Ueda et al.

[11] Patent Number: 4,477,447
[45] Date of Patent: Oct. 16, 1984

[54] 7-ACYLAMINOCEPHALOSPORANIC ACID DERIVATIVES

[75] Inventors: Ikuo Ueda, Toyonaka; Tsutomu Teraji, Osaka; Takao Takaya, Kawanishi; Keiji Takai, Nara; Hisashi Takasugi, Osaka; Fumio Shimojo; Shigetaka Nishino, both of Kawanishi, all of Japan

[73] Assignee: Fujisawa Pharmaceutical Co., Ltd., Osaka, Japan

[21] Appl. No.: 351,858

[22] Filed: Feb. 24, 1982

Related U.S. Application Data

[63] Continuation-in-part of Ser. No. 337,499, Jan. 6, 1982, abandoned, which is a continuation-in-part of Ser. No. 329,861, Dec. 11, 1981, abandoned.

[30] Foreign Application Priority Data

Dec. 15, 1980 [GB] United Kingdom ................. 8040108
Dec. 23, 1980 [JP] Japan ............................... 55-183299
Dec. 30, 1980 [GB] United Kingdom ................. 8041516
Mar. 16, 1981 [GB] United Kingdom ................. 8108135

[51] Int. Cl.³ .................. A61K 31/545; C07D 501/22
[52] U.S. Cl. ..................................... 424/246; 544/22; 544/23
[58] Field of Search ..................... 424/246; 544/22, 23

[56] References Cited

U.S. PATENT DOCUMENTS 4,278,793  7/1981  Durckheimer ........................ 544/23
4,298,529  11/1981  Ueda et al. ............................ 544/28
4,370,326  1/1983  Takaya et al. ........................ 544/22

Primary Examiner—Paul M. Coughlan, Jr.
Attorney, Agent, or Firm—Oblon, Fisher, Spivak, McClelland & Maier

[57] ABSTRACT

This invention relates to novel 7-acylaminocephalosporanic acid derivatives of high antimicrobial activity, to processes for their preparation, and to pharmaceutical compositions comprising said derivatives, said derivatives being of the formula:

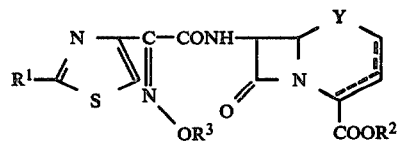

wherein
$R^1$ is amino or protected amino,
$R^2$ is dialkanoyloxy(lower)alkyl; alkyl having one or more substituents selected from the group consisting of hydroxy, protected hydroxy, alkoxy, carboxy, protected carboxy, cycloalkylcarbonyloxy and heterocyclic group; lower alkoxycarbonyloxy(lower)alkyl; azido(lower)alkoxycarbonyloxy(lower)alkyl; aroyloxy(lower)alkyl; higher alkanoyloxy(lower)alkyl; phthalidyl; or phthalidylidene(lower)alkyl,
$R^3$ is lower alkyl,
Y is thio (—S—) or sulfinyl (—S—), and the dotted line represents 2- or 3-cephem nuclei.

3 Claims, No Drawings

7-ACYLAMINOCEPHALOSPORANIC ACID DERIVATIVES

This application is a continuation-in-part of application Ser. No. 337,499, filed Jan. 6, 1982, which in turn is a continuation-in-part of application Ser. No. 329,861, filed Dec. 11, 1981, both now abandoned.

The present invention relates to novel 7-acylaminocephalosporanic acid derivatives and pharmaceutically acceptable salts thereof.

More particularly, it relates to novel 7-acylaminocephalosporanic acid derivatives and pharmaceutically acceptable salts thereof, which have antimicrobial activity, to processes for the preparation thereof, to a pharmaceutical composition comprising the same, and to a method of using the same therapeutically in the treatment of infectious diseases in human being and animals.

Accordingly, one object of the present invention is to provide novel 7-acylaminocephalosporanic acid derivatives and pharmaceutically acceptable salts thereof, which are highly active against a number of pathogenic microorganisms and are useful as antimicrobial agents, especially for oral administration.

Another object of the present invention is to provide processes for the preparation of novel 7-acylaminocephalosporanic acid derivatives and salts thereof.

A further object of the present invention is to provide a pharmaceutical composition comprising, as active ingredients, said 7-acylaminocephalosporanic acid derivatives and pharmaceutically acceptable salts thereof.

Still further object of the present invention is to provide a method of using said 7-acylaminocephalosporanic acid derivatives and pharmaceutically acceptable salts thereof in the treatment of infectious diseases by pathogenic microorganisms in human being and animals.

The object 7-acylaminocephalosporanic acid derivatives having syn configuration are novel and can be represented by the following general formula:

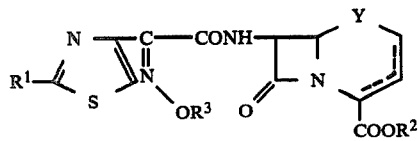
(I)

wherein
R$^1$ is amino or protected amino, and
R$^2$ is dialkanoyloxy(lower)alkyl; alkyl having one or more substituent(s) selected from the groups consisting of hydroxy, protected hydroxy, alkoxy, carboxy, protected carboxy, cycloalkylcarbonyloxy and heterocyclic group; lower alkoxycarbonyloxy(lower)alkyl; azido(lower)alkoxycarbonyloxy(lower)alkyl; aroyloxy(lower)alkyl; higher alkanoyloxy(lower)alkyl; phthalidyl; or phthalidylidene(lower)alkyl,
R$^3$ is lower alkyl,
Y is thio (—S—) or sulfinyl (—SO—), and the dotted line represents 2- or 3-cephem nuclei.

Among the compounds (I), the compounds (Ia) are more useful as antimicrobial agents and can be represented by the following formula:

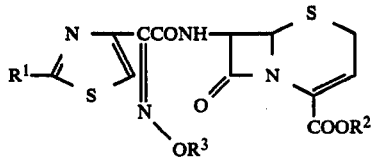
(Ia)

wherein
R$^1$ is amino or protected amino,
R$^2$ is dialkanoyloxy(lower)alkyl; alkyl having one or more substituent(s) selected from the groups consisting of hydroxy, protected hydroxy, alkoxy, carboxy, cycloalkylcarbonyloxy and heterocyclic group; lower alkoxycarbonyloxy(lower)alkyl; azido(lower)alkoxycarbonyloxy(lower)alkyl; aroyloxy(lower)alkyl; higher alkanoyloxy(lower)alkyl; phthalidyl; or phthalidylidene(lower)alkyl, and
R$^3$ is lower alkyl.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

According to the present invention, the object compounds (I) and the pharmaceutically acceptable salts thereof can be prepared by the processes as illustrated by the following reaction schemes.

Process 1:

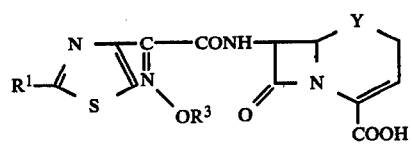
(II)

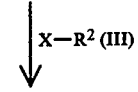

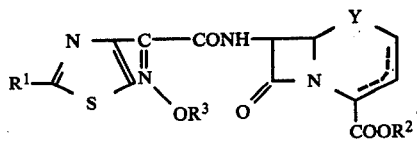
(I)

or a salt thereof

Process 2:

-continued

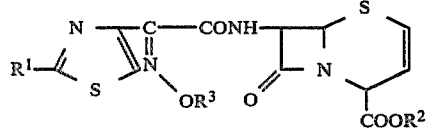

or a salt thereof

| Oxidation

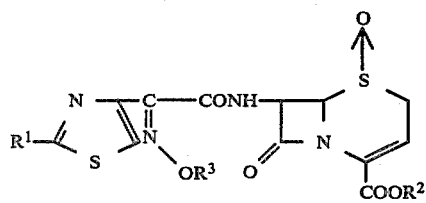

or a salt thereof

Process 3

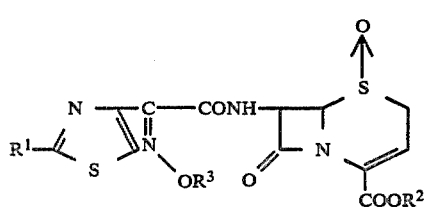

or a salt thereof

| Reduction

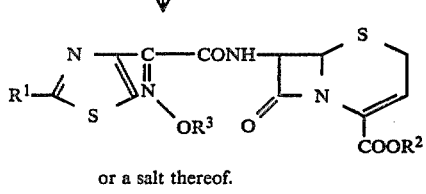

or a salt thereof.

Process 4:

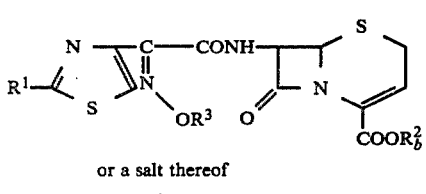

or a salt thereof

| Elimination of carboxy protecting group in $R_a^2$

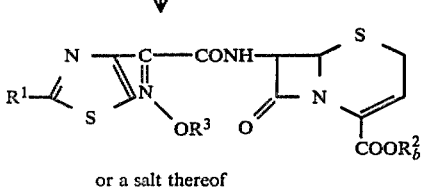

or a salt thereof

Process 5:

-continued

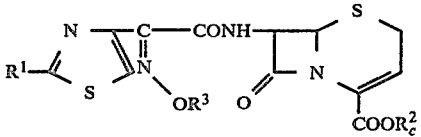

or a salt thereof

| Elimination of hydroxy protecting group in $R_c^2$

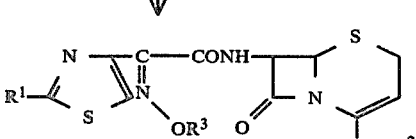

or a salt thereof

Process 6:

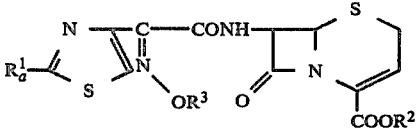

or a salt thereof

| Elimination of amino protecting group in $R_a^2$

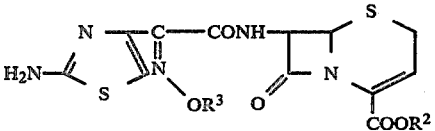

or a salt thereof wherein
$R^1$, $R^2$, $R^3$ and Y are each as defined above,
$R_a^1$ is protected amino,
$R_a^2$ is protected carboxy(lower)alkyl,
$R_b^2$ is carboxy(lower)alkyl,
$R_c^2$ is di(protected hydroxy)-(lower)alkyl, or
$R_d^2$ is dihydroxy(lower)alkyl,
X is hydroxy or its reactive derivative, and the dotted line represents 2- or 3-cephem nuclei.

In the above and subsequent description of the present specification, suitable examples and illustrations of the various definitions to be included within the scope thereof are explained in detail as follows.

The term "lower" is intended to mean a group having 1 to 6 carbon atoms, and the term "higher" is intended to mean a group having 7 to 20 carbon atoms, unless otherwise indicated.

Suitable "protected amino" group may include an amino group substituted by a conventional amino-protective group which is used in penicillin and cephalosporin compounds, for example, acyl as mentioned below, ar(lower)alkyl such as mono-(or di or tri)phenyl(-lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(-lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$-$C_7$)cycloalkanecarbonyl (e.g. cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-trichloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "alkanoyloxy" moiety in the term "dialkanoyloxy(lower)alkyl" may include formyloxy, acetoxy, propionyloxy, butyryloxy, isobutyryloxy, valeryloxy, isovaleryloxy, pivaloyloxy, hexanoyloxy, heptanoyloxy, octanoyloxy, nonanoyloxy, decanoyloxy, or the like, and preferably ($C_1$-$C_{10}$)alkanoyloxy.

Suitable "lower alkyl" moiety in the terms "dialkanoyloxy(lower)alkyl", "protected carboxy(lower)alkyl", "carboxy(lower)alkyl", "di(protected hydroxy)(lower)alkyl" and "dihydroxy(lower)alkyl" may include methyl, ethyl, propyl, isopropyl, butyl, isobutyl, tert-butyl, pentyl, isopentyl, neopentyl, hexyl or the like, and preferably ($C_1$-$C_4$)alkyl.

Suitable "alkyl" may include straight or branched alkyl having 1 to 15 carbon atom(s) such as methyl, ethyl, propyl, isopropyl, butyl, isobutyl, pentyl, isopentyl, neopentyl, hexyl, heptyl, octyl, nonyl, decyl, undecyl, dodecyl, tridecyl, tetradecyl, pentadecyl, or the like, and preferably ($C_1$-$C_{10}$)alkyl.

Suitable "protected hydroxy" and "protected hydroxy" moiety in the term "di(protected hydroxy)(lower)alkyl" may include the hydroxy group is protected with a conventional protecting group, for example, with a ketone compound such as di(lower)alkylketone (e.g. acetone, ethylmethylketone, methyl-n-propylketone, diethylketone, 2-hexanone, 3-hexanone, tert-butylmethylketone, etc.), cyclohexanone, biacetyl, acetylacetone, acetophenone, propiophenone, benzophenone, or the like.

Suitable "alkoxy" may include straight or branched alkoxy having 1 to 15 carbon atom(s) such as methoxy, ethoxy, propoxy, isopropoxy, butoxy, tert-butoxy, pentyloxy, hexyloxy, heptyloxy, octyloxy, nonyloxy, decyloxy, undecyloxy, dodecyloxy, tridecyloxy, tetradecyloxy, pentadecyloxy, or the like and preferably ($C_1$-$C_{12}$)alkoxy.

Suitable "protected carboxy" and "protected carboxy" moiety in the term "protected carboxy(lower)alkyl" may included esterified carboxy such as lower alkoxycarbonyl (e.g. methoxycarbonyl, ethoxycarbonyl, propoxycarbonyl, isopropoxycarbonyl, butoxycarbonyl, tert-butoxycarbonyl, etc.), mono(or di or tri)phenyl(lower)alkoxycarbonyl which may have a nitro group (e.g. benzyloxycarbonyl, 4-nitrobenzyloxycarbonyl, phenethyloxycarbonyl, benzhydryloxycarbonyl, trityloxycarbonyl, etc.), or the like.

Suitable "cycloalkylcarbonyloxy" may include ($C_3$-$C_8$)cycloalkylcarbonyloxy such as ccyclopentylcarbonyloxy, cyclohexylcarbonyloxy, cycloheptylcarbonyloxy or the like, and preferably ($C_5$-$C_6$)cycloalkylcarbonyloxy.

Suitable "heterocyclic group" may include saturated or unsaturated, monocyclic or polycyclic heterocyclic group containing at least one hetero-atom such as an oxygen, sulfur, nitrogen atom, or the like. And, especially preferable heterocyclic group may be heterocyclic group such as unsaturated 3 to 8-membered(more preferably 5 or 6-membered)heteromonocyclic group containing 1 to 4 nitrogen atom(s), for example, pyrrolyl, pyrrolidinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; or the like.

Suitable "lower alkoxycarbonyloxy(lower)alkyl" may include methoxycarbonyloxymethyl, ethoxycarbonyloxymethyl, 2-methoxycarbonyloxyethyl, 1-ethoxycarbonyloxyethyl, 1-isopropoxycarbonyloxyethyl, and the like.

Suitable "azido(lower)alkoxycarbonyloxy(lower)alkyl" may include azidomethoxycarbonyloxymethyl, 2-azidoethoxycarbonyloxymethyl, 1-(2-azidoethoxycarbonyloxy)ethyl, 2-(2-azidoethoxycarbonyloxy)ethyl, and the like.

Suitable "aroyloxy(lower)alkyl" may include benzoyloxy(lower)alkyl (e.g. benzoyloxymethyl, 1-benzoyloxyethyl, etc.), and toluoyloxy(lower)alkyl (e.g. toluoyloxymethyl, 1-toluoyloxyethyl, etc.).

Suitable "higher alkanoyloxy(lower)alkyl" may include 2,3-dimethylpentanoyloxymethyl, tridecanoyloxymethyl, octanoyloxymethyl, tetradecanoyloxymethyl, and tetradecanoyloxyethyl.

Suitable "phthalidylidene(lower)alkyl" may include 3-phthalidylidenemethyl, 1-(3-phthalidylidene)ethyl, 2-(3-phthalidylidene)ethyl, 1-(3-phthalidylidene)propyl, 2-(3-phthalidylidene)propyl, 3-(3-phthalidylidene)propyl, 1-(3-phthalidylidene)butyl, 2-(3-phthalidylidene)butyl, 3-(3-phthalidylidene)butyl, 4-(3-phthalidylidene)butyl, 1-(3-phthalidylidene)heptyl, and the like.

Suitable "reactive derivative of the hydroxy" for X may include an acid residue such as halogen (e.g. chlorine, bromine, iodine, etc.), sulfonate, sulfate, or the like.

Preferable examples of $R^2$ may be:

dialkanoyloxy(lower)alkyl (e.g. diacetoxymethyl, 1,2-diacetoxyethyl, 1,2-dinonanoyloxyethyl, 1,2-dipropionyloxypropyl, 1,3-dipropionyloxypropyl, 1,3-dihexanoyloxypropyl, 1,3-diheptanoyloxypropyl, 1,3-dioctanoyloxypropyl, 1,3-dinonanoyloxypropyl, 1,3-didecanoyloxypropyl, 1,3-dinonanoyloxybutyl, 1,3-dinonanoyloxypentyl, 1,3-dinonanoyloxyhexyl, 2-nonanoyloxy-1-nonanoyloxymethylethyl, etc.), and more preferably di($C_1$-$C_{10}$)alkanoyloxy($C_1$-$C_6$)alkyl;

alkyl (e.g. methyl, ethyl, propyl, isopropyl, butyl, isobutyl, pentyl, isopentyl, neopentyl, hexyl, heptyl, octyl, nonyl, decyl, undecyl, etc.);

dihydroxy(lower)alkyl (e.g. 1,2-dihydroxyethyl, 1,2-dihydroxypropyl, 1,3-dihydroxypropyl, 2,3-dihydroxypropyl, 1,2-dihydroxybutyl, 1,3-dihydroxybutyl, 1,4-dihydroxybutyl, 1,2-dihydroxypentyl, 1,3-dihydroxypentyl, etc.);

di(protected hydroxy)(lower)alkyl such as [2,2-di(lower)alkyl-1,3-dioxolan-4-yl]-(lower)alkyl [e.g. (2,2-dimethyl-1,3-dioxolan-4-yl)methyl, (2,2-dimethyl-1,3-dioxolan-4-yl)ethyl, (2,2-dimethyl-1,3-dioxolan-4-yl)propyl, (2,2-diethyl-1,3-dioxolan-4-yl)methyl, (2,2-dipropyl-1,3-dioxolan-4-yl)butyl, (2-methyl-2-ethyl-1,3-dioxolan-4-yl)hexyl, etc.] or the like;

dialkoxy(lower)alkyl (e.g. dimethoxymethyl, 1,2-dimethoxyethyl, 1,2-dipropoxyethyl, 1,3-dimethoxypropyl, 1,3-diethoxypropyl, 1,3-diisopropoxypropyl, 1,3-ditert-butoxypropyl, 1,3-dipentyloxypropyl, 1,3-diheptyloxypropyl, 1,3-dioctyloxypropyl, 1,3-dinonanyloxypropyl, 1,3-diundecyloxypropyl, 1,3-didodecyloxypropyl, 1,2-dimethoxypropyl, 1,2-dibutoxypropyl, 2,3-dioctyloxypropyl, 1,4-dibutoxybutyl, 2-ethoxy-1-ethoxymethylethyl, 2-isopropoxy-1-isopropoxymethylethyl, 2-butoxy-1-butoxymethylethyl, 2-tert-butoxy-1-tert-butoxymethylethyl, 2-octyloxy-1-octyloxymethylethyl, 2-dodecyloxy-1-dodecyloxymethylethyl, or the like, and more preferably di($C_1$-$C_{12}$)alkoxy($C_1$-$C_6$)alkyl;

carboxy(lower)alkyl (e.g. carboxymethyl, carboxyethyl, 1-carboxypropyl, 2-carboxypropyl, 3-carboxypropyl, 1-carboxybutyl, 2-carboxybutyl, 4-carboxybutyl, 5-carboxypentyl, 6-carboxyhexyl, etc.);

protected carboxy(lower)alkyl such as esterified carboxy(lower)alkyl or the like, and more preferably lower alkoxycarbonyl(lower)alkyl (e.g. methoxycarbonylmethyl, ethoxycarbonylmethyl, propoxycarbonylmethyl, tert-butoxycarbonylmethyl, tert-butoxycarbonylpropyl, 1-tert-butoxycarbonylpropyl, 3-tert-butoxycarbonylpropyl, 5-tert-butoxycarbonylpentyl, etc.), mono(or di or tri)phenyl(lower)alkoxycarbonyl(lower)alkyl which may have a nitro group (e.g. benzyloxycarbonylmethyl, 4-nitrobenzyloxycarbonylmethyl, benzhydryloxycarbonylmethyl, 2-benzyloxycarbonylethyl, 3-(4-nitrobenzyloxycarbonyl)propyl, 3-benzhydryloxycarbonylpropyl, 1-benzhydryloxycarbonylpropyl, 5-benzhydryloxycarbonylpentyl, 5-(4-nitrobenzyloxycarbonyl)pentyl, 6-(4-nitrobenzyloxycarbonyl)hexyl, trityloxycarbonylmethyl, etc.) and the like;

cycloalkylcarbonyloxy(lower)alkyl (e.g. cyclobutylcarbonyloxymethyl, cyclopentylcarbonyloxymethyl, cyclopentylcarbonyloxyethyl, cyclopentylcarbonyloxypropyl, cyclopentylcarbonyloxybutyl, cyclopentylcarbonyloxypentyl, cyclopentylcarbonyloxyhexyl, cyclohexylcarbonyloxymethyl, cyclohexylcarbonyloxyethyl, cyclohexylcarbonyloxybutyl, cyclohexylcarbonyloxypropyl, etc.), and more preferably ($C_5$-$C_6$)cycloalkylcarbonyloxy($C_1$-$C_6$)alkyl;

heterocyclic(lower)alkyl such as unsaturated 5 or 6 membered heteromonocyclic(lower)alkyl containing 1 to 4 nitrogen atoms (e.g. pyrrolylmethyl, imidazolylmethyl, pyridylmethyl, pyridylethyl, pyridylpropyl, pyridylbutyl, pyridylpentyl, pyridylhexyl, pyrimidinylmethyl, pyrimidinylpentyl, triazolylethyl, tetrazolylmethyl, tetrazolylbutyl, tetrazolylpentyl, etc.), and more preferably pyridyl($C_1$-$C_6$)alkyl;

lower alkoxycarbonyloxy(lower)alkyl (e.g. methoxycarbonyloxymethyl, ethoxycarbonyloxymethyl, 2-methoxycarbonyloxyethyl, 1-ethoxycarbonyloxyethyl, 1-isopropoxycarbonyloxyethyl, 1-methoxycarbonyloxyethyl, etc.), and more preferably $C_1$-$C_4$alkoxycarbonyloxy($C_1$-$C_4$)alkyl, and most preferably $C_1$-$C_3$alkoxycarbonyloxy($C_1$-$C_3$)alkyl;

azido(lower)alkoxycarbonyloxy(lower)alkyl (e.g. azidomethoxycarbonyloxymethyl, 2-azidoethoxycarbonyloxymethyl, 1-(2-azidoethoxycarbonyloxy)ethyl, 2-(2-azidoethoxycarbonyloxy)ethyl, etc.), and more preferably azido($C_1$-$C_3$)alkoxycarbonyloxy($C_1$-$C_3$)alkyl;

aroyloxy(lower)alkyl such as benzoyloxy(lower)alkyl (e.g. benzoyloxymethyl, 1-benzoyloxyethyl, etc.), toluoyloxy(lower)alkyl (e.g. toluoyloxymethyl, 1-toluoyloxyethyl, etc.), and the like, and more preferably benzoyloxy($C_1$-$C_3$)alkyl;

higher alkanoyloxy(lower)alkyl (e.g. 2,3-dimethylpentanoyloxymethyl, tridecanoyloxymethyl, octanoyloxymethyl, tetradecanoyloxymethyl, tetradecanoyloxyethyl, etc.), and more preferably ($C_7$-$C_{16}$)alkanoyloxy($C_1$-$C_3$)alkyl;

phthalidylidene(lower)alkyl [e.g. 3-phthalidylidenemethyl, 1-(3-phthalidylidene)ethyl, 2-(3-phthalidylidene)ethyl, 1-(3-phthalidylidene)propyl, 2-(3-phthalidylidene)propyl, 3-(3-phthalidylidene)propyl, 1-(3-phthalidylidene)butyl, 2-(3-phthalidylidene)butyl, 3-(3-phthalidylidene)butyl, 4-(3-phthalidylidene)butyl, 1-(3-phthalidylidene)heptyl, etc.], and more preferably phthalidylidene($C_1$-$C_4$)alkyl, and phthalidyl (e.g. 3-phthalidyl, etc.).

Suitable "lower alkyl" for $R^3$ may include methyl, ethyl, propyl, isopropyl, butyl, isobutyl, tert-butyl, pentyl, hexyl, and the like.

The processes 1 to 6 for the preparation of the object compound (I) of the present invention are explained in detail in the following.

(1) Process 1

The compound (I) or a salt thereof can be prepared by reacting the compound (II) or a salt thereof with an esterifying agent of the formula: X—$R^2$ (III) wherein $R^2$ and X are each as defined above. Suitable salts of the compound (II) can be referred to the ones exemplified for the compound (I).

The reaction can be carried out in the presence of an organic or inorganic base such as alkali metal (e.g. lithium, sodium, potassium etc.), alkaline earth metal (e.g.

calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like, and can also be carried out in the presence of metal iodide (e.g. sodium iodide, etc.).

This reaction is usually carried out in a conventional solvent which does not adversely influence the reaction such as N,N-dimethylformamide, tetrahydrofuran, dimethylsulfoxide, pyridine, dioxane, methanol, ethanol, water, acetone, acetonitrile, chloroform, benzene, methylene chloride, ethylene chloride, ethyl acetate, hexamethylphosphoramide, etc. or a mixture thereof.

In case that alcohol is used as an esterifying agent (III), the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, benzenesulfonyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride or phosgene, molecular sieves, or the like.

The reaction temperature is not critical, and the reaction is usually carried out under cooling to at somewhat elevated temperature.

Some of the starting compound (III) used in Process 1 are new and can be prepared, for example, from the known compounds by the conventional methods. The detailed explanation of these methods are disclosed in the following Preparations 2 to 6.

(2) Process 2

The object compound (Ic) or a salt thereof can be prepared by oxidizing the compound (Ib) or a salt thereof.

Suitable salts of the compound (Ib) can be referred to the ones exemplified for the compound (I).

The present oxidation reaction can be carried out by a conventional method which is applied for the transformation of —S— into

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitril, chloroform, methylene chloride, tetrahydrofuran, ethyl acetate or any other solvents which do not adversely affect the reaction.

The reaction temperature is not critical and the reaction is preferably carried out under cooling or at ambient temperature.

(3) Process 3

The compound (Ia) or a salt thereof can be prepared by reducing the compound (Ic) or a salt thereof.

Suitable salts of the compound (Ic) can be referred to the ones as exemplified for the compound (I).

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present invention is usually carried out in a solvent such as acetone, dioxane, acetonitrile, benzene, hexane, chloroform, methylene chloride, ethylene chloride, tetrahydrofuran, ethyl acetate, or any other solvents which do not adversely affect the reaction.

The reaction temperature is not critical and the reaction is usually carried out under cooling or at ambient temperature.

(4) Process 4

The compound (Ie) or a salt thereof can be prepared by subjecting the compound (Id) or a salt thereof to elimination reaction of the carboxy-protective group in $R_a{}^2$.

Suitable method for the elimination reaction may include conventional one such as hydrolysis, reduction, and the like.

(I) For hydrolysis

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the protective group to be eliminated, for example, this hydrolysis can preferably be applied to the cases that the carboxy protecting group is substituted or unsubstituted lower alkyl, substituted or unsubstituted mono(or di or tri)phenyl(lower)alkyl or the like.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(II) For Reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.) copper catalysts (e.g. reduced copper, Raney copper, Ullman copper, etc.) and the like.

The reduction manner can be selected according to the kinds of the protective group to be removed, for example, the chemical reduction can preferably be applied to the cases that the carboxy protecting a group is halo(lower)alkyl or the like, and catalytic reduction can preferably be applied to the cases that the carboxy protecting group is substituted or unsubstituted mono(or di or tri)phenyl(lower)alkyl, or the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The methods thus explained may be selected depending upon the kind of the protective group to be eliminated.

(5) Process 5

The compound (Ig) or a salt thereof can be prepared by subjecting the compound (If) or a salt thereof to elimination reaction of the hydroxy-protecting group in $R_c{}^2$.

The suitable salt of the compound (If) can be referred to ones exemplified for the compound (I).

The reaction is carried out by a conventional method such as hydrolysis, reduction, and the like.

The method of hydrolysis and reduction, and the reaction conditions (e.g. reaction temperature, solvent, etc.) are substantially the same as those illustrated for elimination of the carboxy-protecting group in Process 4.

The present invention includes, within the scope, cases that protected amino group(s) and/or the protected carboxy group(s) are transformed into the corresponding free amino group(s) and/or free carboxy group(s), respectively during the reaction.

(6) Process 6

The compound (Ii) or a salt thereof can be prepared by subjecting the compound (Ih) or a salt thereof to the elimination reaction of the amino-protecting group in $R_a{}^1$.

The suitable salt of the compound (Ih) can be referred to ones exemplified for the compound (I).

This reaction is carried out by a conventional method such as hydrolysis, reduction, and the like.

The method of hydrolysis and reduction, and the reaction conditions (e.g. reaction temperature, solvent, etc.) are substantially the same as those illustrated for elimination of carboxy protecting group in Process 4.

The present invention includes, within the scope, cases that protected carboxy group(s), and/or the protected hydroxy group(s) are transformed into the corresponding free carboxy group(s) and/or free hydroxy group(s), respectively, during the reaction.

The compounds (I), wherein $R^2$ is alkyl, may be prepared by the processes as mentioned above, and the detailed explanation therefor are given in Examples mentioned below.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration.

For therapeutic administration, the object compounds (I) and the pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral and external administration.

The object compounds (I) and the pharmaceutically acceptable salts thereof possess high antimicrobial activities and are to be used for injection administration, suppository administration and oral administration, especially for the oral administration, the preparation of which are explained, for example, as mentioned below. The pharmaceutical preparations may be in solid form such as tablet, granule, powder, capsule, or liquid form such as solution, suspension, syrup, emulsion, lemonade and the like. If needed, there may be included in the above preparations auxiliary substances, stabilizing agents, wetting agents and any of the other additives, which are commonly and conventionally used in the cephalosporin preparations, such as lactose magnesium stearate, terra alba, sucrose, corn starch, talc, stearic acid, gelatin, agar, pectin, peanut oil, olive oil, cacao butter, ethylene glycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following examples are given for the purpose of illustrating the present invention.

Preparation 1 n-Nonanoyl chloride (23 g) was dropwise added to a stirred solution of glycerin (6.0 g) in dry pyridine (60 ml) at 0° to 5° C. over 30 minutes. The mixture was stirred at the same temperature for an hour, and then allowed to stand at room temperature overnight. The resultant mixture was poured into ice water (300 ml), and extracted with ethyl acetate (50 ml×2). The extract was washed with water (10 ml), 10% aqueous hydrochloric acid and a saturated aqueous solution of sodium chloride (40 ml) in turn, and then dried over anhydrous magnesium sulfate. The solution was evaporated in vacuo, and the residue was subjected to column chromatography on silica gel (636 g) with a mixture of chloroform and acetone (30:1). The eluate was evaporated in vacuo to give 1,3-di-n-nonanoyloxy-2-propanol, mp 30°-31° C.

IR (Film): 3480, 1745 cm$^{-1}$.

NMR (CDCl$_3$, δ): 0.7–2.0 (30H, m), 2.33 (4H, t, J=7 Hz), 2.87 (1H, broad s), 3.9–4.4 (5H, broad s).

Preparation 2

Bromoacetyl chloride (113 g) was dropwise added to a stirred solution of 4-nitrobenzyl alcohol (9.2 g) and pyridine (10 ml) in dry tetrahydrofuran (100 ml) at 0° C. over 50 minutes. The mixture was stirred at 0° to 5° C. for 30 minutes, and evaporated in vacuo. The residue was dissolved in a mixture of chloroform (70 ml) and water (20 ml), and then the organic layer was separated. The organic layer was washed with a diluted aqueous hydrochloric acid and water in turn, and then dried over anhydrous magnesium sulfate. The solution was evaporated in vacuo, and the residue was recrystallized from methanol to give crystals (6.74 g) of 4-nitrobenzyl bromoacetate.

IR (Nujol): 1760, 1610 cm$^{-1}$.

NMR (CDCl$_3$, δ): 4.13 (2H, s), 5.32 (2H, s), 7.52 (2H, d, J=9 Hz), 8.23 (2H, d, J=9 Hz).

Preparation 3

The following compounds were obtained according to a similar manner to that of Preparation 2.
(1) 4-Nitrobenzyl 6-bromohexanoate IR (Film): 1740, 1605 cm$^{-1}$.

NMR (CDCl$_3$, δ): 1.1–2.1 (6H, m), 2.41 (2H, t, J=6 Hz), 3.40 (2H, t, J=6 Hz), 5.20 (2H, s), 7.47 (2H, d, J=9 Hz), 8.20 (2H, d, J=9 Hz).
(2) 4-Nitrobenzyl 4-chlorobutyrate IR (Film): 1740 cm$^{-1}$.

NMR (CDCl$_3$, δ): 1.9–2.3 (2H, m), 2.6 (2H, t, J=7 Hz), 3.7 (2H, t, J=6 Hz), 5.3 (2H, s), 7.5 (2H, d, J=9 Hz), 8.2 (2H, d, J=9 Hz).

Preparation 4

Sodium iodide (3.5 g) was slowly added to a stirred solution of 4-nitrobenzyl bromoacetate (5.0 g) in acetone (50 ml) at room temperature over 5 minutes, and the solution was stirred at the same temperature for 2.25 hours. The resultant mixture was evaporated in vacuo, and the residue was dissolved in a mixture of ethyl acetate (40 ml) and water (15 ml). The organic layer was separated, washed with a saturated aqueous solution of sodium chloride and an aqueous solution of sodium thiosulfate in turn, and then dried over anhydrous magnesium sulfate. After the solution was evaporated in vacuo, the residue was allowed to stand in a refrigerator overnight, and triturated with methanol (10 ml) to give crystals (5.25 g) of 4-nitrobenzyl iodoacetate, mp 62.5° to 63.5° C.

IR (Nujol): 1735 cm$^{-1}$.

NMR (CDCl$_3$, δ): 3.80 (2H, s), 5.28 (2H, s), 7.55 (2H, d, J=9 Hz), 8.25 (2H, d, J=9 Hz).

Preparation 5

The following compounds were obtained according to a similar manner to that of Preparation 4.
(1) 4-Nitrobenzyl 6-iodohexanoate IR (Film): 1740 cm$^{-1}$.

NMR (CDCl$_3$, δ): 1.2–2.1 (6H, m), 2.40 (2H, t, J=6 Hz), 3.15 (2H, t, J=6 Hz), 5.17 (2H, s), 7.43 (2H, d, J=9 Hz), 8.15 (2H, d, J=9 Hz).
(2) 4-Nitrobenzyl 4-iodobutyrate IR (Film): 1745 cm$^{-1}$.

NMR (CDCl$_3$, δ): 1.9–2.4 (2H, m), 2.56 (2H, t, J=6 Hz), 3.27 (2H, t, J=6 Hz), 5.27 (2H, s), 7.53 (2H, d, J=9 Hz), 8.23 (2H, d, J=9 Hz).

Preparation 6 p-Toluenesulfonyl chloride (1.2 g) was added to a stirred solution of 2,3-di-n-octyloxy-1-propanol (930 mg) in dried pyridine (10 ml) at 2° C. over 7 minutes. The reaction mixture was stirred at 0° to 5° C. for 2 hours and at room temperature overnight. The resultant solution was poured into ice water (50 ml) and extracted with ethyl acetate (40 ml). The extract was washed with dil. hydrochloric acid (20 ml) and a saturated aqueous solution of sodium chloride (20 ml) in turn, and dried over anhydrous magnesium sulfate. The solvent was evaporated under reduced pressure to give oil (920 mg) of 2,3-di-n-octyloxy-1-propyl p-toluenesulfonate.

IR (Film): 1600, 1465, 1365, 1190, 1180 cm$^{-1}$.

NMR (CDCl$_3$, δ): 0.65–2.0 (30H, m), 2.42 (3H, s), 3.2–3.75 (7H, m), 3.83–4.30 (2H, m), 7.27 (2H, d, J=8 Hz), 7.75 (2H, d, J=8 Hz).

Preparation 7

Sodium iodide (4.07 g) was added to a stirred solution of 2,3-di-n-octyloxy-1-propyl p-toluenesulfonate (860 mg) in acetone (14 ml) at room temperature and heated under reflux for 11 hours. The resultant mixture was evaporated under reduced pressure, and the residue was dissolved in a mixture of water (20 ml) and diethyl ether (10 ml). The aqueous solution was separated and extracted with diethyl ether, and then the organic layer and the extract were combined. The organic solution was washed with a saturated aqueous solution of sodium chloride twice, and dried over anhydrous magnesium sulfate. The solvent was evaporated under reduced pressure to give oil (620 mg) of 2,3-di-n-octyloxy-1-propyl iodide.

IR (Film): 1465, 1120 cm$^{-1}$.

NMR (CDCl$_3$, δ): 0.67–1.9 (30H), 3.20–3.70 (9H, m).

EXAMPLE 1 n-Butyl iodide (13.4 g) and triethylamine (6.1 ml) were added to a solution of 7-[2-(2-formamidothiazol-4-yl)-2-methoxyiminoacetamido]-3-cephem-4-carboxylic acid (syn isomer, 10.0 g) in dry N,N-dimethylformamide (100 ml) under ice cooling, and stirred at 40° C. for 3.5 hours. The resultant solution was poured into a mixture of ethyl acetate (300 ml) and water (500 ml), and adjusted to pH 1.5 with 6N hydrochloric acid. After separating the organic layer, the aqueous layer was extracted with ethyl acetate (100 ml×2). The organic layer and the extract were combined and washed with a saturated aqueous solution of sodium bicarbonate, 5% aqueous solution of sodium thiosulfate and a saturated aqueous solution of sodium chloride in turn. After treating the solution with activated charcoal, the solution was dried over anhydrous magnesium sulfate.

The solution was evaporated in vacuo, and the residue was triturated with diethyl ether (100 ml). The precipitates were collected by filtration, washed with diethyl ether (20 ml) twice and dried over phosphorus pentoxide in vacuo to give n-butyl 7-[2-(2-formamidothiazol-4-yl)-2-methoxyiminoacetamido]-3-cephem-4-carboxylate (syn isomer, 7.6 g).

IR (Nujol): 3250, 3170, 3050, 1790, 1780, 1770, 1725, 1700, 1660, 1635, 1565, 1550 cm$^{-1}$.

NMR (DMSO-d$_6$, δ): 0.88 (3H, t, J=6 Hz), 1.13–1.92 (4H, broad), 3.62 (2H, d, J=4 Hz), 3.88 (3H, s), 4.17 (2H, t, J=6 Hz), 5.10 (1H, d, J=5 Hz), 5.85 (1H, dd, J=5 Hz, 8 Hz), 6.47 (1H, t, J=4 Hz), 7.35 (1H, s), 8.45 (1H, s), 9.63 (1H, d, J=8 Hz), 12.82 (1H, s).

EXAMPLE 2

Molecular sieves (3 Å) (10 g) was added to a solution of 7-[2-(2-formamidothiazol-4-yl)-2-methoxyiminoacetamido]-3-cephem-4-carboxylic acid (syn isomer, 5 g) in dry pyridine (45 ml), and stirred at room temperature for 40 minutes. Dry tetrahydrofuran (15 ml) and 2,2-dimethyl-4-hydroxymethyl-1,3-dioxolane (1.6 g) were added to the solution, and then chilled with ice water. After adding dicyclohexylcarbodiimide (3.8 g) to the solution, the solution was stirred at 0° to 3° C. under nitrogen gas atmosphere for 6 hours. The resultant mixture was added to ice water (300 ml) and filtered out. The filtrate was extracted with ethyl acetate (300 ml) twice. Ice-water was added to the extract and the solution was adjusted to pH 3 to 4 with 3N hydrochloric acid and washed with a saturated aqueous solution of sodium chloride. The organic layer was adjusted to pH 7 to 8 with a saturated aqueous solution of sodium bicarbonate and washed with water. The solution was dried over anhydrous magnesium sulfate. The solution was evaporated in vacuo to give brown oil (3.8 g). The oil was purified by column chromatography on silica gel to give (2,2-dimethyl-1,3-dioxolan-4-yl)methyl 7-[2-(2-formamidothiazol-4-yl)-2-methoxyiminoacetamido]-3-cephem-4-carboxylate (syn isomer, 2.4 g).

IR (Nujol): 3500, 3250, 3200, 3160, 3040, 1780, 1710, 1680, 1630 cm$^{-1}$.

NMR (CDCl$_3$, δ): 1.37 (3H, s), 1.43 (3H, s), 3.5–3.7 (2H, m), 3.96 (3H, s), 3.6–4.6 (5H, m), 5.07 (1H, d, J=5 Hz), 6.02 (1H, dd, J=5 Hz, 9 Hz), 6.5–6.8 (1H, m), 7.85 (1H, d, J=9 Hz), 8.57 (1H, s), 11.7 (1H, broad s).

EXAMPLE 3

Molecular sieves (3 Å) (15 g) was added to a solution of 7-[2-(2-formamidothiazol-4-yl)-2-methoxyiminoacetamido]-3-cephem-4-carboxylic acid (syn isomer, 8.2 g) in dry pyridine (80 ml), and stirred at room temperature for 30 minutes. Dry tetrahydrofuran (15 ml) and 2-hydroxymethylpyridine (2.2 g) were added to the solution and chilled with ice water. After adding dicyclohexylcarbodiimide (6.2 g) to the solution, the solution was stirred at 0° to 3° C. under nitrogen gas atmosphere for 4 hours and additionally at room temperature for 14 hours. Ethyl acetate (200 ml) was added to the resultant mixture and filtered out. The filtrate was adjusted to pH 3 to 4 with 3N hydrochloric acid. After removing the organic layer from the resultant solution, ethyl acetate (400 ml) was added to the aqueous solution. The solution was adjusted to pH 8 to 9 with a saturated aqueous solution of sodium bicarbonate. The aqueous layer was extracted with a mixed solution of ethyl acetate (200 ml) and tetrahydrofuran (200 ml). The organic layer was combined and washed with a saturated aqueous solution of sodium chloride, dried over anhydrous magnesium sulfate, and evaporated in vacuo to give orange oil (6.0 g). The oil was purified by column chromatography on silica gel to give pure oil (3.5 g). The oil was pulverized with diisopropyl ether to give pale yellow powder (2.8 g) of 2-pyridylmethyl 7-[2-(2-Formamidothiazol-4-yl)-2-methoxyiminoacetamido]-3-cephem-4-carboxylate (syn isomer).

IR (Nujol): 3250, 3150, 3050, 1760, 1730, 1690, 1650 cm$^{-1}$.

NMR (DMSO-d$_6$, δ): 3.5–3.8 (2H, m), 3.93 (3H, s), 5.20 (1H, d, J=5 Hz), 5.37 (2H, s), 5.98 (1H, dd, J=5 Hz, 8 Hz), 6.5–6.8 (1H, m), 7.3–8.1 (4H, m), 8.5–8.8 (2H, m), 9.75 (1H, d, J=8 Hz).

EXAMPLE 4

Dicyclohexylcarbodiimide (6.5 g) was added to a stirred solution of 7-[2-(2-formamidothiazol-4-yl)-2-methoxyiminoacetamido]-3-cephem-4-carboxylic acid (syn isomer, 8.6 g) and 2-n-nonanoyloxy-1-n-nonanoyloxymethylethanol (7.8 g) in a mixture of dry pyridine (80 ml) and dry tetrahydrofuran (25 ml) at 3° C., and then stirred at 0° to 5° C. for 4 hours and allowed to stand at room temperature overnight. The resultant mixture was poured into ice water (450 ml) and extracted with ethyl acetate (450 ml). Water (50 ml) was added to the extract and adjusted to pH 2 to 3 with 20% sulfuric acid. The organic layer was separated, washed with a saturated aqueous solution of sodium chloride (100 ml×2) and an aqueous solution of sodium bicarbonate in turn, and dried over anhydrous magnesium sulfate. After removing the solution in vacuo, the residue was subjected to column chromatography on silica gel (370 g) with a mixture of chloroform and acetone (5:1). The eluate was evaporated in vacuo to give powder (4.62 g) of 2-n-nonanoyloxy-1-n-nonanoyloxymethylethyl 7-[2-(2-formamidothiazol-4-yl)-2-methoxyiminoacetamido]-3-cephem-4-carboxylate (syn isomer).

IR (Nujol): 3330, 3260, 1785, 1740, 1680 cm$^{-1}$.

NMR (CDCl$_3$, δ): 0.7–1.8 (30H, m), 2.30 (4H, t, J=6 Hz), 3.4–3.6 (2H, broad s), 3.92 (3H, s), 4.1–4.4 (4H, m), 5.06 (1H, d, J=5 Hz), 5.3–5.5 (1H, m), 6.03 (1H, q, J=5

Hz, 8 Hz), 6.48–6.65 (1H, m), 7.16 (1H, s), 7.85 (1H, d, J=8 Hz), 8.52 (1H, s).

EXAMPLE 5

7-[2-(2-Aminothiazol-4-yl)-2-methoxyiminoacetamido]-3-cephem-4-carboxylic acid (syn isomer, 6.0 g) was dissolved in a mixed solution of dry dimethylsulfoxide (90 ml) and dry dimethylformamide (30 ml). After adding triethylamine (1.58 g) to the stirred solution at 9° C. over 2 minutes, iodomethyl cyclohexanecarboxylate (4.2 g) was added thereto with stirring over 5 minutes, and then stirred under ice cooling for 35 minutes. Ice water (500 ml) was added to the resultant solution and extracted with ethyl acetate three times. The solution was subsequently washed with a diluted aqueous solution of sodium bicarbonate, an aqueous solution of sodium thiosulfate and a saturated aqueous solution of sodium chloride, and dried over anhydrous magnesium sulfate. The solution was evaporated in vacuo, and the residue was purified by column chromatography on silica gel (100 g) with a mixed solution of chloroform and acetone (10:3). The eluate was evaporated in vacuo to give the purified residue. The residue was pulverized with diisopropyl ether and dried in vacuo to give cyclohexylcarbonyloxymethyl 7-[2-(2-aminothiazol-4-yl)-2-methoxyiminoacetamido]-3-cephem-4-carboxylate (syn isomer, 4.0 g).

IR (Nujol): 3410, 3300, 1775, 1745, 1670, 1620 cm$^{-1}$.

NMR (CDCl$_3$, $\delta$): 1.0–2.5 (11H, m), 3.5–3.7 (2H, m), 4.05 (3H, s), 5.08 (1H, d, J=5 Hz), 5.83 (2H, s), 5.92 (2H, s), 6.10 (1H, ABq, J=9 Hz, 5 Hz), 6.6–6.9 (1H, m), 6.75 (1H, s), 8.00 (1H, d, J=9 Hz)

To a cold solution of the above compound in ethyl acetate, was added dropwise hydrochloric acid with stirring, and then the precipitates were collected by filtration to give cyclohexylcarbonyloxymethyl 7-[2-(2-aminothiazol-4-yl)-2-methoxyiminoacetamido]-3-cephem-4-carboxylate hydrochloride (syn isomer).

mp 134°–139° C.

(IR Nujol): 3250, 3150, 2700, 1780, 1745, 1670, 1630 cm$^{-1}$.

NMR (DMSO-d$_6$, $\delta$): 1.0–2.1 (10H, m), 3.6–3.9 (2H, m), 3.93 (3H, s), 5.2 (1H, d, J=5 Hz), 5.5–6.5 (7H, m), 6.6–6.8 (1H, m), 6.93 (1H, s), 9.8 (1H, d, J=8 Hz).

EXAMPLE 6

To a solution of sodium 7-[2-(2-aminothiazol-4-yl)-2-methoxyiminoacetamido]-3-cephem-4-carboxylate (syn isomer, 5.0 g) in N,N-dimethylformamide (100 ml) was added tert-butyl bromoacetate (2.9 g), and the solution was stirred for 3 hours at ambient temperature. The reaction mixture was extracted with ethyl acetate. The organic layer was washed with a saturated aqueous solution of sodium bicarbonate and water in turn, and dried over anhydrous magnesium sulfate. The solution was evaporated in vacuo to give tert-butoxycarbonylmethyl 7-[2-(2-aminothiazol-4-yl)-2-methoxyiminoacetamido]-3-cephem-4-carboxylate (syn isomer, 3.2 g), mp 188°–190° C. (dec.).

IR (Nujol): 3250, 3080, 1775, 1730, 1654, 1620 cm$^{-1}$.

NMR (DMSO-d$_6$, $\delta$): 1.45 (9H, s), 3.65 (2H, m), 3.85 (3H, s), 4.70 (2H, s), 5.15 (1H, d, J=5 Hz), 5.87 (1H, dd, J=5 Hz, 8 Hz), 6.67 (1H, m), 6.72 (1H, s), 9.60 (1H, d, J=8 Hz).

EXAMPLE 7

A mixture of 7-[2-(2-formamidothiazol-4-yl)-2-methoxyiminoacetamido]-3-cephem-4-carboxylic acid (syn isomer, 6.0 g) and molecular sieves (20 g) in dry pyridine (60 ml) was stirred at 0° to 5° C. for an hour, and 2-n-octyloxy-1-n-octyloxymethylethanol [4.6 g] was added thereto. Benzenesulfonyl chloride (2.6 g) was dropwise added to the stirred solution at −5° to −3° C. over 30 minutes, and then stirred at 0° C. for an hour. The resultant mixture was poured into the crushed ice (300 g), adjusted to pH 1 to 2 with 20% sulfuric acid, and then extracted with ethyl acetate (300 ml). The extract was washed with a saturated aqueous solution of sodium chloride, an aqueous solution of sodium bicarbonate and a saturated aqueous solution of sodium chloride in turn, and dried over anhydrous magnesium sulfate. The solution was evaporated under reduced pressure, and the residue was subjected to column chromatography on silica gel (200 g) with a mixture of chloroform and methanol (20:1). The eluate was evaporated in vacuo to give powder [3.1 g] of 2-n-octyloxy-1-n-octyloxymethylethyl 7-[2-(2-formamidothiazol-4-yl)-2-methoxyiminoacetamido]-2-cephem-4-carboxylate (syn isomer).

IR (Nujol): 3270, 1785, 1750, 1700, 1665 cm$^{-1}$.

NMR (CDCl$_3$, $\delta$): 0.6–2.1 (30H, m), 3.2–3.8 (8H, m), 4.0 (3H, s), 4.9–5.2 (2H, m), 5.3 (1H, d, J=5 Hz), 5.7–6.7 (3H, m), 7.2 (1H, s), 8.0 (1H, d, J=8 Hz), 8.6 (1H, s), 11.8 (1H, s).

EXAMPLE 8

Dicyclohexylcarbodiimide (3.96 g) was added to a stirred solution of 7-[2-(2-formamidothiazol-4-yl)-2-methoxyiminoacetamido]-3-cephem-4-carboxylic acid (syn isomer, 6.58 g] and 2-n-dodecyloxy-1-n-dodecyloxymethylethanol (8.23 g) in a mixture of dry pyridine (60 ml) and dry tetrahydrofuran (20 ml) at 3° C., and then stirred at 0° to 5° C. for 4.75 hours and further at room temperature for an hour. The resultant mixture was poured into ice water (350 ml) and extracted with ethyl acetate (500 ml). Water (50 ml) was added to the extract and adjusted to pH 2 to 3 with 20% sulfuric acid. The organic layer was separated and washed with a saturated aqueous solution of sodium chloride (100 ml×2) and an aqueous solution of sodium bicarbonate in turn, and dried over anhydrous magnesium sulfate. After evaporating the solution in vacuo, the residue was subjected to column chromatography on silica gel (266 g) with a mixture of chloroform and methanol (20:1). The eluate was evaporated in vacuo to give powder [6.24 g] of 2-n-dodecyloxy-1-n-dodecyloxymethylethyl 7-[2-(2-formamidothiazol-4-yl)-2-methoxyiminoacetamido]-2-cephem-4-carboxylate (syn isomer).

IR (Nujol): 3250, 1795, 1735, 1695, 1670 cm$^{-1}$.

NMR (CDCl$_3$, $\delta$): 0.7–2.1 (46H, m), 3.3–3.8 (8H, m), 4.0 (3H, s), 4.9–5.4 (3H, m), 5.7–6.7 (3H, m), 7.17 (1H, s), 7.8 (1H, d, J=8 Hz), 8.5 (1H, s), 11.7 (1H, broad s).

EXAMPLE 9

The following examples were obtained according to similar manners to those of Examples 1 to 8.
(1) n-Hexyl 7-[2-(2-formamidothiazol-4-yl)-2-methoxyiminoacetamido]-3-cephem-4-carboxylate (syn isomer).

IR (Nujol): 3250, 3170, 3050, 1790, 1740, 1720, 1700, 1660, 1640, 1570, 1550 cm$^{-1}$.

NMR (DMSO-d$_6$, $\delta$): 0.82 (3H, t, J=6 Hz), 1.00–1.77 (8H, broad), 3.57 (2H, d, J=4 Hz), 3.87 (3H, s), 4.13 (2H, t, J=6 Hz), 5.10 (1H, d, J=5 Hz), 5.87 (1H, dd, J=5 Hz, 8 Hz), 6.48 (1H, t, J=4 Hz), 7.37 (1H, s), 8.48 (1H, s), 9.65 (1H, d, J=8 Hz), 12.73 (1H, s).

(2) n-Octyl 7-[2-(2-formamidothiazol-4-yl)-2-methoxyiminoacetamido]-3-cephem-4-carboxylate (syn isomer).

IR (Nujol): 3250, 3150, 3050, 1790, 1730, 1690, 1550 cm$^{-1}$.

NMR (DMSO-d$_6$, δ): 0.92 (3H, t, J=6 Hz), 1.10–1.90 (12H, broad), 3.60 (2H, d, J=4 Hz), 3.90 (3H, s), 4.17 (2H, t, J=6 Hz), 5.13 (1H, d, J=5 Hz), 5.87 (1H, dd, J=5 Hz, 8 Hz), 6.50 (1H, t, J=4 Hz), 7.22 (1H, s), 8.50 (1H, s), 9.67 (1H, d, J=8 Hz), 12.77 (1H, s).

(3) n-Decyl 7-[2-(2-formamidothiazol-4-yl)-2-methoxyiminoacetamido]-3-cephem-4-carboxylate (syn isomer).

IR (Nujol): 3250, 3150, 3050, 1790, 1730, 1690, 1660, 1550 cm$^{-1}$.

NMR (DMSO-d$_6$, δ): 0.83 (3H, t, J=6 Hz), 1.13–1.83 (16H, broad), 3.58 (2H, d, J=4 Hz), 3.88 (3H, s), 4.17 (2H, t, J=6 Hz), 5.13 (1H, d, J=5 Hz), 5.87 (1H, dd, J=5 Hz, 8 Hz), 6.50 (1H, t, J=4 Hz), 7.37 (1H, s), 8.50 (1H, s), 9.67 (1H, d, J=8 Hz).

(4) 2-n-Butoxy-1-n-butoxymethylethyl 7-[2-(2-formamidothiazol-4-yl)-2-methoxyiminoacetamido]-2-cephem-4-carboxylate (syn isomer), mp 82° to 84° C.

IR (Nujol): 3310, 1790, 1740, 1690 (broad) cm$^{-1}$.

NMR (CDCl$_3$, δ): 0.7–1.1 (6H, m), 1.1–2.7 (8H, m), 3.3–3.7 (8H, m), 4.0 (3H, s), 4.8–5.4 (3H, m), 5.7–6.6 (3H, m), 7.2 (1H, s), 7.8 (1H, d, J=9 Hz), 8.5 (1H, s), 11.7 (1H, broad s).

(5) 4-Nitrobenzyloxycarbonylmethyl 7-[2-(2-aminothiazol-4-yl)-2-methoxyiminoacetamido]-3-cephem-4-carboxylate (syn isomer).

IR (Nujol): 3450, 3320, 1775, 1740, 1680 cm$^{-1}$.

NMR (CDCl$_3$, δ): 3.56 (2H, broad s), 4.02 (3H, s), 4.83 (2H, s), 5.05 (1H, d, J=5 Hz), 5.28 (2H, s), 5.75 (2H, broad s), 6.06 (1H, q, J=8 Hz, 5 Hz), 6.66 (1H, t, J=4 Hz), 6.72 (1H, s), 7.48 (2H, d, J=9 Hz), 7.93 (1H, d, J=8 Hz), 8.20 (2H, d, J=9 Hz).

(6) 5-(4-Nitrobenzyloxycarbonyl)pentyl 7-[2-(2-aminothiazol-4-yl)-2-methoxyiminoacetamido]-3-cephem-4-carboxylate (syn isomer).

IR (Nujol): 3400, 3300, 1770, 1720, 1670 cm$^{-1}$.

NMR (CDCl$_3$, δ): 1.2–2.0 (6H, m), 2.40 (2H, t, J=6 Hz), 3.35–3.65 (2H, m), 4.00 (3H, s), 4.23 (2H, t, J=6 Hz), 5.02 (1H, d, J=5 Hz), 5.17 (2H, s), 5.73 (2H, broad s), 6.05 (1H, q, J=9 Hz, 5 Hz), 6.4–6.6 (1H, m), 6.70 (1H, s), 7.45 (2H, d, J=10 Hz), 7.83 (1H, d, J=9 Hz), 8.15 (2H, d, J=10 Hz).

(7) 3-(4-Nitrobenzyloxycarbonyl)propyl 7-[2-(2-aminothiazol-4-yl)-2-methoxyiminoacetamido]-3-cephem-4-carboxylate (syn isomer), mp. 98° to 100° C.

IR (Nujol): 3400, 3300, 1775, 1725, 1675 cm$^{-1}$.

NMR (CDCl$_3$, δ): 1.8–2.3 (2H, m), 2.58 (2H, t, J=6 Hz), 3.4–3.6 (2H, m), 4.0 (3H, s), 4.3 (2H, t, J=6 Hz), 5.02 (1H, d, J=5 Hz), 5.18 (2H, s), 5.63 (2H, broad s), 6.03 (1H, q, J=9 Hz, 5 Hz), 6.52 (1H, q, J=6 Hz, 4 Hz), 6.70 (1H, s), 7.47 (2H, d, J=8 Hz), 7.70 (1H, d, J=9 Hz), 8.13 (2H, d, J=8 Hz).

(8) 1-Diphenylmethoxycarbonylpropyl 7-[2-(2-aminothiazol-4-yl)-2-methoxyiminoacetamido]-3-cephem-4-carboxylate (syn isomer), mp 133° to 138° C. (dec.).

IR (Nujol): 3300, 1776, 1730, 1672 cm$^{-1}$.

NMR (DMSO-d$_6$, δ): 0.92 (3H, m), 1.90 (2H, m), 3.62 (2H, m), 3.83 (3H, s), 5.07 (1H, d), 5.17 (1H, m), 5.80 (1H, m), 6.60 (1H, m), 6.68 (1H, s), 6.80 (1H, s), 7.3 (10H, m), 9.53 (1H, d, J=8 Hz).

(9) n-Hexyl 7-[2-(2-aminothiazol-4-yl)-2-methoxyiminoacetamido]-3-cephem-4-carboxylate (syn isomer).

IR (Nujol): 3500, 3250, 3100, 3000–2200, 1780, 1730, 1660, 1630, 1540 cm$^{-1}$.

NMR (DMSO-d$_6$, δ): 0.87 (3H, t, J=6 Hz), 1.17–1.90 (8H, broad), 3.65 (2H, d, J=4 Hz), 3.90 (3H, s), 4.23 (2H, t, J=6 Hz), 5.17 (1H, d, J=5 Hz), 5.90 (1H, dd, J=5 Hz, 8 Hz), 6.57 (1H, d, J=4 Hz), 6.80 (1H, s), 7.23 (2H, s), 9.67 (1H, d, J=8 Hz).

(10) n-Octyl 7-[2-(2-aminothiazol-4-yl)-2-methoxyiminoacetamido]-3-cephem-4-carboxylate (syn isomer).

IR (Nujol): 3500, 3260, 3100, 3000–2200, 1780, 1730, 1680, 1630, 1540 cm$^{-1}$.

NMR (DMSO-d$_6$, δ): 0.87 (3H, t, J=6 Hz), 1.10–1.83 (12H, broad), 3.63 (2H, d, J=4 Hz), 3.90 (3H, s), 4.23 (2H, t, J=6 Hz), 5.17 (1H, d, J=5 Hz), 5.90 (1H, dd, J=5 Hz, 8 Hz), 6.58 (1H, t, J=4 Hz), 6.80 (1H, s), 7.23 (2H, s), 9.67 (1H, d, J=8 Hz).

(11) n-Decyl 7-[2-(2-aminothiazol-4-yl)-2-methoxyiminoacetamido]-3-cephem-4-carboxylate (syn isomer).

IR (Nujol): 3500, 3260, 3100, 3000–2000, 1780, 1730, 1660, 1630, 1540 cm$^{-1}$.

NMR (DMSO-d$_6$, δ): 0.87 (3H, t, J=6 Hz), 1.13–1.83 (16H, broad), 3.63 (2H, d, J=4 Hz), 3.87 (3H, s), 4.20 (2H, t, J=6 Hz), 5.15 (1H, d, J=5 Hz), 5.87 (1H, dd, J=5 Hz, 8 Hz), 6.57 (1H, t, J=4 Hz), 6.80 (1H, s), 7.23 (2H, s), 9.63 (1H, d, J=8 Hz).

(12) 2-Pyridylmethyl 7-[2-(2-aminothiazol-4-yl)-2-methoxyiminoacetamido]-3-cephem-4-carboxylate (syn isomer).

IR (Nujol): 3550, 3400, 3300, 3150, 1780, 1730, 1690, 1670, 1650, 1630 cm$^{-1}$.

NMR (DMSO-d$_6$, δ): 3.5–3.8 (2H, m), 3.87 (3H, s), 5.16 (1H, d, J=5 Hz), 5.34 (2H, s), 5.89 (1H, dd, J=5 Hz, 8 Hz), 6.4–7.0 (1H, m), 6.74 (1H, s), 7.0–8.6 (6H, m), 9.59 (1H, d, J=8 Hz).

(13) 2-n-Octyloxy-1-n-octyloxymethylethyl 7-[2-(2-aminothiazol-4-yl)-2-methoxyiminoacetamido]-3-cephem-4-carboxylate (syn isomer).

IR (Nujol): 3400, 3300, 1770, 1725, 1670 cm$^{-1}$.

NMR (CDCl$_3$, δ): 0.6–2.0 (30H, m), 3.3–3.8 (10H, m), 4.0 (3H, s), 5.05 (1H, d, J=5 Hz), 5.1–5.4 (1H, m), 5.75 (2H, broad s), 6.07 (1H, q, J=5 Hz, 9 Hz), 6.3–6.7 (1H, m), 7.27 (1H, s), 7.90 (1H, d, J=9 Hz).

(14) 2-n-Dodecyloxy-1-n-dodecyloxymethylethyl 7-[2-(2-aminothiazol-4-yl)-2-methoxyiminoacetamido]-3-cephem-4-carboxylate (syn isomer), mp 97° to 98° C.

IR (Nujol): 3420, 3250, 1760, 1725, 1650 cm$^{-1}$.

NMR (CDCl$_3$, δ): 0.7–1.8 (46H, m), 3.3–3.8 (10H, m), 4.05 (3H, s), 5.05 (1H, d, J=5 Hz), 5.27 (1H, m), 5.6 (2H, broad s), 6.05 (1H, q, J=5 Hz, 9 Hz), 6.47–6.67 (1H, m), 6.78 (1H, (1H, s), 7.70 (1H, d, J=9 Hz).

(15) 2-n-Butoxy-1-butoxymethylethyl 7-[2-(2-aminothiazol-4-yl)-2-methoxyiminoacetamido]-3-cephem-4-carboxylate (syn isomer), mp 83° to 85° C.

IR (Nujol): 3400, 3300, 1770, 1725, 1675 cm$^{-1}$.

NMR (CDCl$_3$, δ): 0.92 (6H, t, J=6 Hz), 1.1–1.7 (8H, m), 3.2–3.8 (10H, m), 4.0 (3H, s), 5.02 (1H, d, J=5 Hz), 5.24 (1H, m), 5.7–6.2 (3H, m), 6.52 (1H, broad s), 6.71 (1H, s), 7.97 (1H, d, J=8 Hz).

To a cold solution of the above compound in ethyl acetate, was added dropwise hydrochloric acid with stirring, and then the precipitates were collected by filtration to give 2-n-butoxy-1-n-butoxymethylethyl 7-[2-(2-aminothiazol-4-yl)-2-methoxyiminoacetamido]-3-cephem-4-carboxylate hydrochloride (syn isomer). mp 90°–95° C.

IR (Nujol): 3250, 3150, 2700, 1780, 1725, 1665, 1630 cm$^{-1}$.

NMR (CDCl$_3$, δ): 0.92 (6H, t, J=6 Hz), 1.1–1.8 (8H, m), 3.2–3.9 (10H, m), 4.1 (3H, s) 4.9–5.5 (2H, m), 5.7–6.2 (1H, m), 6.4–6.8 (1H, m), 7.03 (1H, s), 8.3 (1H, d, J=8 Hz).

(16) 2-n-Nonanoyloxy-1-n-nonanoyloxymethylethyl 7-[2-(2-aminothiazol-4-yl)-2-methoxyiminoacetamido]-3-cephem-4-carboxylate (syn isomer).

IR (Nujol): 3420, 3320, 1780, 1735, 1675 cm$^{-1}$.

NMR (CDCl$_3$, δ): 0.7–2.0 (30H, m), 2.1–2.6 (4H, m), 3.4–3.7 (2H, m), 4.05 (3H, s), 4.15–4.50 (4H, m), 5.10 (1H, d, J=5 Hz), 5.2–5.8 (3H, m), 6.10 (1H, q, J=5 Hz, 8 Hz), 6.5–6.7 (1H, m), 6.76 (1H, s), 7.93 (1H, d, J=8 Hz).

(17) 2,3-Dihydroxypropyl 7-[2-(2-aminothiazol-4-yl)-2-methoxyiminoacetamido]-3-cephem-4-carboxylate (syn isomer).

IR (Nujol): 3400, 3300, 1770, 1720, 1660 cm$^{-1}$.

NMR (DMSO-d$_6$, δ): 3.3–5.0 (9H, m), 3.82 (3H, s), 5.02 (1H, d, J=5 Hz), 5.87 (1H, dd, J=5 Hz, 8 Hz), 6.5–6.8 (1H, m), 6.68 (1H, s), 7.12 (2H, broad s), 9.50 (1H, d, J=8 Hz).

(18) n-Butyl 7-[2-(2-aminothiazol-4-yl)-2-methoxyiminoacetamido]-3-cephem-4-carboxylate (syn isomer).

IR (Nujol): 3500–2200, 1780, 1730, 1680, 1620, 1540 cm$^{-1}$.

NMR (DMSO-d$_6$, δ): 0.9 (3H, t, J=6 Hz), 1.13–1.80 (4H, broad), 3.63 (2H, d, J=4 Hz), 3.85 (3H, t), 4.18 (2H, t, J=6 Hz), 5.12 (1H, d, J=5 Hz), 5.83 (1H, dd, J=5 Hz, 8 Hz), 6.51 (1H, t, J=4 Hz), 6.73 (1H, s), 7.18 (2H, s), 9.60 (1H, d, J=8 Hz).

EXAMPLE 10

A solution of 3-chloroperbenzoic acid (0.9 g) in methylene chloride (10 ml) was dropwise added to a stirred solution of 2-n-octyloxy-1-n-octyloxymethylethyl 7-[2-(2-formamidothiazol-4-yl)-2-methoxyiminoacetamido]-2-cephem-4-carboxylate (syn isomer, 3.0 g) in methylene chloride (30 ml) at −7° to −3° C. over 30 minutes, and then stirred at 0° C. for 35 minutes. The resultant mixture was washed with a diluted aqueous solution of sodium bicarbonate and saturated aqueous solution of sodium chloride in turn, and dried over anhydrous magnesium sulfate. After removing the solvent from the solution in vacuo, the residue was subjected to column chromatography on silica gel (120 g) with a mixture of chloroform and methanol (20:1). The eluate was evaporated in vacuo to give powder [2.44 g] of 2-n-octyloxy-1-n-octyloxymethylethyl 7-[2-(2-formamidothiazol-4-yl)-2-methoxyiminoacetamido]-3-cephem-4-carboxylate-1-oxide (syn isomer).

IR (Nujol): 3200 (broad), 1795, 1730, 1695, 1650 cm$^{-1}$.

NMR (CDCl$_3$, δ): 0.7–1.8 (30H, m), 3.2–3.8 (10H, m), 3.90 (3H, s), 4.62 (1H, d, J=5 Hz), 5.0–5.4 (1H, m), 6.0–6.4 (2H, m), 7.22 (1H, s), 8.22 (1H, d, J=9 Hz), 8.43 (1H, s).

EXAMPLE 11

The following compounds were obtained according to a similar manner to that of Example 10.
(1) 2-n-Dodecyloxy-1-n-dodecyloxymethylethyl 7-[2-(2-formamidothiazol-4-yl)-2-methoxyiminoacetamido]-3-cephem-4-carboxylate-1-oxide (syn isomer), mp 179° to 182° C.

IR (Nujol): 3500, 3230, 1790, 1725, 1685, 1655 cm$^{-1}$.

NMR (CDCl$_3$, δ): 0.7–2.0 (46H, m), 3.2–3.3 (10H, m), 3.9 (3H, s), 4.6 (1H, d, J=4 Hz), 5.0–5.4 (1H, m), 6.0–6.4 (2H, m), 7.3 (1H, s), 8.2 (1H, d, J=8 Hz), 8.5 (1H, s).

(2) 2-n-Butoxy-1-n-butoxymethylethyl 7-[2-(2-formamidothiazol-4-yl)-2-methoxyiminoacetamido]-3-cephem-4-carboxylate-1-oxide (syn isomer), mp 186° to 188° C.

IR (Nujol): 3500, 3260, 3170, 1790, 1735, 1695, 1665 cm$^{-1}$.

NMR (CDCl$_3$, δ): 0.75–1.75 (14H, m), 3.30–3.85 (10H, m), 3.93 (3H, s), 4.72 (1H, d, J=5 Hz), 5.2–5.5 (1H, m), 6.15–6.55 (2H, m), 7.3 (1H, s), 8.38 (1H, d, J=8 Hz), 8.60 (1H, s), 11.8 (1H, broad s).

EXAMPLE 12

2,2,2-Trifluoroacetic anhydride (2.12 g) was dropwise added to a stirred solution of 2-n-octyloxy-1-n-octyloxymethylethyl 7-[2-(2-formamidothiazol-4-yl)-2-methoxyiminoacetamido]-3-cephem-4-carboxylate-1-oxide (syn isomer, 2.34 g) and sodium iodide (1.56 g) in dry acetone (40 ml) at 0° to 5° C. over 45 minutes, and stirred at 0° to 5° C. for 2 hours. The resultant mixture was poured into ice water (200 ml), and then extracted with ethyl acetate (110 ml). The extract was washed with an aqueous solution of sodium thiosulfate, an aqueous solution of sodium bicarbonate and a saturated aqueous solution of sodium chloride in turn, and then dried over anhydrous magnesium sulfate. After evaporating the solution in vacuo, the residue was subjected to column chromatography, on silica gel (100 g) with a mixture of chloroform and methanol (20:1). The eluate was evaporated in vacuo to give powder (1.57 g) of 2-n-octyloxy-1-n-octyloxymethylethyl 7-[2-(2-formamidothiazol-4-yl)-2-methoxyiminoacetamido]-3-cephem-4-carboxylate (syn isomer, 1.57 g).

IR (Nujol): 3200 (broad), 1785, 1725, 1680, 1650 cm$^{-1}$.

NMR (CDCl$_3$, δ): 0.7–1.7 (30H, m), 3.3–3.8 (10H, m), 4.0 (3H, s), 5.07 (1H, d, J=5 Hz), 5.1–5.4 (1H, m), 6.05 (1H, q, J=5 Hz, 8 Hz), 6.5–6.7 (1H, m), 7.22 (1H, s), 7.85 (1H, d, J=8 Hz), 8.53 (1H, s).

EXAMPLE 13

The following compounds were obtained according to a similar manner to that of Example 12.
(1) 2-n-Dodecyloxy-1-n-dodecyloxymethylethyl 7-[2-(2-formamidothiazol-4-yl)-2-methoxyiminoacetamido]-3-cephem-4-carboxylate (syn isomer).

IR (Nujol): 3350, 3300, 3200, 1780, 1730, 1700, 1660 cm$^{-1}$.

NMR (CDCl$_3$, δ): 0.7–2.0 (46H, m), 3.3–3.8 (10H, m), 3.95 (3H, s), 5.05 (1H, d, J=5 Hz), 5.22 (1H, m), 6.02 (1H, q, J=5 Hz, 9 Hz), 6.47–6.70 (1H, m), 7.13 (1H, s), 7.77 (1H, d, J=9 Hz), 8.50 (1H, s).

(2) 2-n-Butoxy-1-n-butoxymethylethyl 7-[2-(2-formamidothiazol-4-yl)-2-methoxyiminoacetamido]-3-cephem-4-carboxylate (syn isomer), mp 83° to 87° C.

IR (Nujol): 3250, 1785, 1735, 1695, 1665 cm$^{-1}$.

NMR (CDCl$_3$, δ): 0.65–1.8 (14H, m), 3.30–3.83 (10H, m), 3.93 (3H, s), 5.03 (1H, d, J=5 Hz), 5.23 (1H, m), 6.00 (1H, q, J=5 Hz, 8 Hz), 6.43–6.73 (1H, m), 7.20 (1H, s), 7.80 (1H, d, J=8 Hz), 8.50 (1H, s), 11.8 (1H, broad s).

EXAMPLE 14

A suspension of 4-nitrobenzyloxycarbonylmethyl 7-[2-(2-aminothiazol-4-yl)-2-methoxyiminoacetamido]-

3-cephem-4-carboxylate (syn isomer, 1.34 g) and 10% palladium on carbon (0.7 g) in tetrahydrofuran (50 ml) and methanol (15 ml) was subjected to catalytic reduction under hydrogen atmosphere at 1 atm., until the uptake of hydrogen ceased. After removing the insoluble substance by filtration, the filtrate was concentrated in vacuo. The residue was triturated with ethyl acetate to give powder (0.35 g) of carboxymethyl 7-[2-(2-aminothiazol-4-yl)-2-methoxyiminoacetamido]-3-cephem-4-carboxylate (syn isomer), mp>250° C.

IR (Nujol): 3600, 3410, 3260, 1770, 1660 cm$^{-1}$.

NMR (DMSO-d$_6$, δ): 3.5–3.8 (2H, broad d), 3.85 (3H, s), 4.73 (2H, s), 5.15 (1H, d, J=5 Hz), 5.87 (1H, q, J=8 Hz, 5 Hz), 6.55–6.87 (2H, m), 6.75 (1H, s), 7.2 (2H, broad s), 9.60 (1H, d, J=8 Hz).

EXAMPLE 15

To a solution of anisole (5 ml) and trifluoroacetic acid (6 ml) was added tert-butoxycarbonylmethyl 7-[2-(2-aminothiazol-4-yl)-2-methoxyiminoacetamido]-3-cephem-4-carboxylate (syn isomer, 1.5 g) with stirring at ambient temperature. The reaction mixture was stirred for an hour at the same temperature. Then the resultant solution was dropwise added to diisopropyl ether (150 ml). The precipitates were collected by filtration and washed with diisopropyl ether. The precipitates were dissolved in an aqueous solution of sodium bicarbonate. The aqueous solution was adjusted to pH 2.5 with conc. hydrochloric acid. The precipitates were collected by filtration, washed with water and dried over phosphorus pentoxide under reduced pressure to give carboxymethyl 7-[2-(2-aminothiazol-4-yl)-2-methoxyiminoacetamido]-3-cephem-4-carboxylate (syn isomer, 0.85 g), IR and NMR spectra of which were the same as those of the object compound of Example 14.

EXAMPLE 16

The following compounds were obtained according to similar manners to those of Examples 14 and 15.

(1) 5-Carboxypentyl 7-[2-(2-aminothiazol-4-yl)-2-methoxyiminoacetamido]-3-cephem-4-carboxylate (syn isomer), mp 120° to 140° C.

IR (Nujol): 3400 (shoulder), 3280, 3170 (shoulder), 1770, 1715, 1670 cm$^{-1}$.

NMR (DMSO-d$_6$, δ): 1.2–1.9 (6H, m), 2.20 (2H, t, J=6 Hz), 3.60 (2H, broad d, J=4 Hz), 3.83 (3H, s), 4.16 (2H, t, J=5 Hz), 5.10 (1H, d, J=5 Hz), 5.82 (1H, q, J=5 Hz, 8 Hz), 6.5 (1H, t, J=4 Hz), 6.72 (1H, s), 7.15 (2H, broad s), 9.57 (1H, d, J=8 Hz).

(2) 3-Carboxypropyl 7-[2-(2-aminothiazol-4-yl)-2-methoxyiminoacetamido]-3-cephem-4-carboxylate (syn isomer).

IR (Nujol): 3400 (shoulder), 3280, 3170, 1770, 1720, 1665 cm$^{-1}$.

NMR (DMSO-d$_6$, δ): 1.7–2.2 (2H, m), 2.36 (2H, t, J=6 Hz), 3.66 (2H, broad d, J=4 Hz), 3.90 (3H, s), 4.26 (2H, t, J=6 Hz), 5.17 (1H, d, J=5 Hz), 5.90 (1H, q, J=5 Hz, 8 Hz), 6.60 (1H, t, J=4 Hz), 6.80 (1H, s), 7.20 (2H, broad s), 9.70 (1H, d, J=8 Hz).

(3) 1-Carboxypropyl 7-[2-(2-aminothiazol-4-yl)-2-methoxyiminoacetamido]-3-cephem-4-carboxylate (syn isomer), mp 145° to 154° C. (dec.).

IR (Nujol): 3300, 1776, 1724, 1666 cm$^{-1}$.

NMR (DMSO-d$_6$, δ): 0.95 (3H, t, J=6 Hz), 1.85 (2H, quintet, J=6 Hz), 3.67 (2H, m), 3.87 (3H, s), 4.95 (1H, m), 5.13 (1H, d, J=5 Hz), 5.83 (1H, m), 6.60 (1H, m), 6.73 (1H, s), 9.55 (1H, d, J=8 Hz).

EXAMPLE 17

12N Hydrochloric acid (1.4 ml) was added to a solution of (2,2-dimethyl-1,3-dioxolan-4-yl)methyl 7-[2-(2-formamidothiazol-4-yl)-2-methoxyiminoacetamido]-3-cephem-4-carboxylate (syn isomer, 1.8 g) in methanol (40 ml), and stirred at room temperature for 2 hours. After adding ice water (200 ml) to the resultant solution, the solution was adjusted to pH 7 to 8 with a saturated aqueous solution of sodium bicarbonate. The solution was extracted with a mixed solution of ethyl acetate (200 ml) and tetrahydrofuran (100 ml) twice. The extract was washed with a saturated aqueous solution of sodium chloride and dried over anhydrous magnesium sulfate. The solution was evaporated in vacuo to give brown oil (1.2 g). The oil was purified by column chromatography on neutral alumina to give yellow oil (0.7 g). The oil was pulverized with diethyl ether to give pale yellow powder (0.5 g) of 2,3-dihydroxypropyl 7-[2-(2-aminothiazol-4-yl)-2-methoxyiminoacetamido]-3-cephem-4-carboxylate (syn isomer).

IR (Nujol): 3400, 3300, 1770, 1720, 1660 cm$^{-1}$.

NMR (DMSO-d$_6$, δ): 3.3–5.0 (9H, m), 3.82 (3H, s), 5.02 (1H, d, J=5 Hz), 5.87 (1H, dd, J=5 Hz, 8 Hz), 6.5–6.8 (1H, m), 6.68 (1H, s), 7.12 (2H, broad s), 9.50 (1H, d, J=8 Hz).

To a cold solution of the above compound in ethyl acetate, was added dropwise hydrochloric acid with stirring, and then the precipitates were collected by filtration to give 2,3-dihydroxypropyl 7-[2-(2-aminothiazol-4-yl)-2-methoxyiminoacetamido]-3-cephem-4-carboxylate hydrochloride (syn isomer).

IR (Nujol): 3250(broad), 1770, 1720, 1650, 1630 cm$^{-1}$.

EXAMPLE 18

Conc-Hydrochloric acid (4 ml) was dropwise added to a suspension of n-butyl 7-[2-(2-formamidothiazol-4-yl)-2-methoxyiminoacetamido]-3-cephem-4-carboxylate (syn isomer, 7.5 g) in methanol (120 ml) over 5 minutes under ice cooling, and stirred at room temperature for 4.25 hours. The resultant solution was poured into chilled water (75 ml), and adjusted to pH 5.5 with 4N aqueous solution of sodium hydroxide at 5° C. After treating the solution with activated charcoal (0.38 g), the solution was concentrated in vacuo. The aqueous residue was stirred under ice cooling for 30 minutes. The precipitates were collected by filtration, washed with water (10 ml×2), and then dried over phosphorus pentoxide to give yellow powder (6.55 g) of n-butyl 7-[2-(2-aminothiazol-4-yl)-2-methoxyiminoacetamido]-3-cephem-4-carboxylate (syn isomer).

IR (Nujol): 3500–2200, 1780, 1730, 1680, 1620, 1540 cm$^{-1}$.

NMR (DMSO-d$_6$, δ): 0.9 (3H, t, J=6 Hz), 1.13–1.80 (4H, broad), 3.63 (2H, d, J=4 Hz), 3.85 (3H, s), 4.18 (2H, t, J=6 Hz), 5.12 (1H, d, J=5 Hz), 5.83 (1H, dd, J=5 Hz, 8 Hz), 6.51 (1H, t, J=4 Hz), 6.73 (1H, s), 7.18 (2H, s), 9.60 (1H, d, J=8 Hz).

EXAMPLE 19

The following compounds were obtained according to similar manners to those of Examples 17 and 18.

(1) n-Hexyl 7-[2-(2-aminothiazol-4-yl)-2-methoxyiminoacetamido]-3-cephem-4-carboxylate (syn isomer).

IR (Nujol): 3500, 3250, 3100, 3000–2200, 1780, 1730, 1660, 1630, 1540 cm$^{-1}$.

NMR (DMSO-d$_6$, δ): 0.87 (3H, t, J=6 Hz), 1.17–1.90 (8H, broad), 3.65 (2H, d, J=4 Hz), 3.90 (3H, s), 4.23 (2H, t, J=6 Hz), 5.17 (1H, d, J=5 Hz), 5.90 (1H, dd, J=5 Hz, 8 Hz), 6.57 (1H, t, J=4 Hz), 6.80 (1H, s), 7.23 (2H, s), 9.67 (1H, d, J=8 Hz).

(2) n-Octyl 7-[2-(2-aminothiazol-4-yl)-2-methoxyiminoacetamido]-3-cephem-4-carboxylate (syn isomer).

IR (Nujol): 3500, 3260, 3100, 3000–2200, 1780, 1730, 1680, 1630, 1540 cm$^{-1}$.

NMR (DMSO-d$_6$, δ): 0.87 (3H, t, J=6 Hz), 1.10–1.83 (12H, broad), 3.63 (2H, d, J=4 Hz), 3.90 (3H, s), 4.23 (2H, t, J=6 Hz), 5.17 (1H, d, J=5 Hz), 5.90 (1H, dd, J=5 Hz, 8 Hz), 6.58 (1H, t, J=4 Hz), 6.80 (1H, s), 7.23 (2H, s), 9.67 (1H, d, J=8 Hz).

(3) n-Decyl 7-[2-(2-aminothiazol-4-yl)-2-methoxyiminoacetamido]-3-cephem-4-carboxylate (syn isomer).

IR (Nujol): 3500, 3260, 3100, 3000–2000, 1780, 1730, 1660, 1630, 1540 cm$^{-1}$.

NMR (DMSO-d$_6$, δ): 0.87 (3H, t, J=6 Hz), 1.13–1.83 (16H, broad), 3.63 (2H, d, J=4 Hz), 3.87 (3H, s), 4.20 (2H, t, J=6 Hz), 5.15 (1H, d, J=5 Hz), 5.87 (1H, dd, J=5 Hz, 8 Hz), 6.57 (1H, t, J=4 Hz), 6.80 (1H, s), 7.23 (2H, s), 9.63 (1H, d, J=8 Hz).

(4) 2-Pyridylmethyl 7-[2-(2-aminothiazol-4-yl)-2-methoxyiminoacetamido]-3-cephem-4-carboxylate (syn isomer).

IR (Nujol): 3550, 3400, 3300, 3150, 1780, 1730, 1690, 1670, 1650, 1630 cm$^{-1}$.

NMR (DMSO-d$_6$, δ): 3.5–3.8 (2H, m), 3.87 (3H, s), 5.16 (1H, d, J=5 Hz), 5.34 (2H, s), 5.89 (1H, dd, J=5 Hz, 8 Hz), 6.4–7.0 (1H, m), 6.74 (1H, s), 7.0–8.6 (6H, m), 9.59 (1H, d, J=8 Hz).

(5) 2-n-Octyloxy-1-n-octyloxymethylethyl 7-[2-(2-aminothiazol-4-yl)-2-methoxyiminoacetamido]-3-cephem-4-carboxylate (syn isomer).

IR (Nujol): 3400, 3300, 1770, 1725, 1670 cm$^{-1}$.

NMR (CDCl$_3$, δ): 0.6–2.0 (30H, m), 3.3–3.8 (10H, m), 4.0 (3H, s), 5.05 (1H, d, J=5 Hz), 5.1–5.4 (1H, m), 5.75 (2H, broad s), 6.07 (1H, q, J=5 Hz, 9 Hz), 6.3–6.7 (1H, m), 7.27 (1H, s), 7.90 (1H, d, J=9 Hz).

(6) 2-n-Dodecyloxy-1-n-dodecyloxymethylethyl 7-[2-(2-aminothiazol-4-yl)-2-methoxyiminoacetamido]-3-cephem-4-carboxylate (syn isomer), mp 97° to 98° C.

IR (Nujol): 3420, 3250, 1760, 1725, 1650 cm$^{-1}$.

NMR (CDCl$_3$, δ): 0.7–1.8 (46H, m), 3.3–3.8 (10H, m), 4.05 (3H, s), 5.05 (1H, d, J=5 Hz), 5.27 (1H, m), 5.6 (2H, broad s), 6.05 (1H, q, J=5 Hz, 9 Hz), 6.47–6.67 (1H, m), 6.78 (1H, s), 7.70 (1H, d, J=9 Hz).

(7) 2-n-Butoxy-1-n-butoxymethylethyl 7-[2-(2-aminothiazol-4-yl)-2-methoxyiminoacetamido]-3-cephem-4-carboxylate (syn isomer), mp 83° to 85° C.

IR (Nujol): 3400, 3300, 1770, 1725, 1675 cm$^{-1}$.

NMR (CDCl$_3$, δ): 0.92 (6H, t, J=6 Hz), 1.1–1.7 (8H, m), 3.2–3.8 (10H, m), 4.0 (3H, s), 5.02 (1H, d, J=5 Hz), 5.24 (1H, m), 5.7–6.2 (3H, m), 6.52 (1H, s), 6.71 (1H, s), 7.97 (1H, d, J=8 Hz).

(8) 2-n-Nonanoyloxy-1-n-nonanoyloxymethylethyl 7-[2-(2-aminothiazol-4-yl)-2-methoxyiminoacetamido]-3-cephem-4-carboxylate (syn isomer).

IR (Nujol): 3420, 3320, 1780, 1735, 1675 cm$^{-1}$.

NMR (CDCl$_3$, δ): 0.7–2.0 (30H, m), 2.1–2.6 (4H, m), 3.4–3.7 (2H, m), 4.05 (3H, s), 4.15–4.50 (4H, m), 5.10 (1H, d, J=5 Hz), 5.2–5.8 (3H, m), 6.10 (1H, q, J=5 Hz, 8 Hz), 6.5–6.7 (1H, m), 6.76 (1H, s), 7.93 (1H, d, J=8 Hz).

(9) 4-Nitrobenzyloxycarbonylmethyl 7-[2-(2-aminothiazol-4-yl)-2-methoxyiminoacetamido]-3-cephem-4-carboxylate (syn isomer).

IR (Nujol): 3450, 3320, 1775, 1740, 1680 cm$^{-1}$.

NMR (CDCl$_3$, δ): 3.56 (2H, broad s), 4.02 (3H, s), 4.83 (2H, s), 5.05 (1H, d, J=5 Hz), 5.28 (2H, s), 5.75 (2H, broad s), 6.06 (1H, q, J=8 Hz, 5 Hz), 6.66 (1H, t, J=4 Hz), 6.72 (1H, s), 7.48 (2H, d, J=9 Hz), 7.93 (1H, d, J=8 Hz), 8.20 (2H, d, J=9 Hz).

(10) 5-(4-Nitrobenzyloxycarbonyl)pentyl 7-[2-(2-aminothiazol-4-yl)-2-methoxyiminoacetamido]-3-cephem-4-carboxylate (syn isomer).

IR (Nujol): 3400, 3300, 1770, 1720, 1670 cm$^{-1}$.

NMR (CDCl$_3$, δ): 1.2–2.0 (6H, m), 2.40 (2H, t, J=6 Hz), 3.35–3.65 (2H, m), 4.00 (3H, s), 4.23 (2H, t, J=6 Hz), 5.02 (1H, d, J=5 Hz), 5.17 (2H, s), 5.73 (2H, broad s), 6.05 (1H, q, J=9 Hz, 5 Hz), 6.4–6.6 (1H, m), 6.70 (1H, s), 7.45 (2H, d, J=10 Hz), 7.83 (1H, d, J=9 Hz), 8.15 (2H, d, J=10 Hz).

(11) 3-(4-Nitrobenzyloxycarbonyl)propyl 7-[2-(2-aminiothiazol-4-yl)-2-methoxyiminoacetamido]-3-cephem-4-carboxylate (syn isomer), mp 98° to 100° C.

IR (Nujol): 3400, 3300, 1775, 1725, 1675 cm$^{-1}$.

NMR (CDCl$_3$, δ): 1.8–2.3 (2H, m), 2.58 (2H, t, J=6 Hz), 3.4–3.6 (2H, m), 4.0 (3H, s), 4.3 (2H, t, J=6 Hz), 5.02 (1H, d, J=5 Hz), 5.18 (2H, s), 5.63 (2H, broad s), 6.03 (1H, q, J=9 Hz, 5 Hz); 6.52 (1H, q, J=6 Hz, 4 Hz), 6.70 (1H, s), 7.47 (2H, d, J=8 Hz), 7.70 (1H, d, J=9 Hz), 8.13 (2H, d, J=8 Hz).

(12) tert-Butoxycarbonyloxymethyl 7-[2-(2-aminothiazol-4-yl)-2-methoxyiminoacetamido]-3-cephem-4-carboxylate (syn isomer), mp 188° to 190° C. (dec.).

IR (Nujol): 3250, 3080, 1775, 1730, 1654, 1620 cm$^{-1}$.

NMR (DMSO-d$_6$, δ): 1.45 (9H, s), 3.65 (2H, m), 3.85 (3H, s), 4.70 (2H, s), 5.15 (1H, d, J=5 Hz), 5.87 (1H, dd, J=5 Hz, 8 Hz), 6.67 (1H, m), 6.72 (1H, s), 9.60 (1H, d, J=8 Hz).

(13) 1-Diphenylmethoxycarbonylpropyl 7-[2-(2-aminothiazol-4-yl)-2-methoxyiminoacetamido]-3-cephem-4-carboxylate (syn isomer), mp 133° to 138° C. (dec.).

IR (Nujol): 3300, 1776, 1730, 1672 cm$^{-1}$.

NMR (DMSO-d$_6$, δ): 0.92 (3H, m), 1.90 (2H, m), 3.62 (2H, m), 3.83 (3H, s), 5.07 (1H, m), 5.17 (1H, m), 5.80 (1H, m), 6.60 (1H, m), 6.68 (1H, s), 6.80 (1H, s), 7.3 (10H, m), 9.53 (1H, d, J=8 Hz).

(14) 5-Carboxypentyl 7-[2-(2-aminothiazol-4-yl)-2-methoxyiminoacetamido]-3-cephem-4-carboxylate (syn isomer), mp 120° to 140° C.

IR (Nujol): 3400 (shoulder), 3280, 3170 (shoulder), 1770, 1715, 1670 cm$^{-1}$.

NMR (DMSO-d$_6$, δ): 1.2–1.9 (6H, m), 2.20 (2H, t, J=6 Hz), 3.60 (2H, broad d, J=4 Hz), 3.83 (3H, s), 4.16 (2H, t, J=5 Hz), 5.10 (1H, d, J=5 Hz), 5.82 (1H, q, J=5 Hz, 8 Hz), 6.5 (1H, t, J=4 Hz), 6.72 (1H, s), 7.15 (2H, broad s), 9.57 (1H, d, J=8 Hz).

(15) 3-Carboxypropyl 7-[2-(2-aminothiazol-4-yl)-2-methoxyiminoacetamido]-3-cephem-4-carboxylate (syn isomer).

IR (Nujol): 3400 (shoulder), 3280, 3170, 1770, 1720, 1665 cm$^{-1}$.

NMR (DMSO-d$_6$, δ): 1.7–2.2 (2H, m), 2.36 (2H, t, J=6 Hz), 3.66 (2H, broad d, J=4 Hz), 3.90 (3H, s), 4.26 (2H, t, J=6 Hz), 5.17 (1H, d, J=5 Hz), 5.90 (1H, q, J=5 Hz, 8 Hz), 6.60 (1H, t, J=4 Hz), 6.80 (1H, s), 7.20 (2H, broad s), 9.70 (1H, d, J=8 Hz).

(16) 1-Carboxypropyl 7-[2-(2-aminothiazol-4-yl)-2-methoxyiminoacetamido]-3-cephem-4-carboxylate (syn isomer), mp 145° to 154° C. (dec.).

IR (Nujol): 3300, 1776, 1724, 1666 cm$^{-1}$.

NMR (DMSO-d$_6$, δ): 0.95 (3H, t, J=6 Hz), 1.85 (2H, quintet, J=6 Hz), 3.67 (2H, m), 3.87 (3H, s), 4.95 (1H, m), 5.13 (1H, d, J=5 Hz), 5.83 (1H, m), 6.60 (1H, m), 6.73 (1H, s), 9.55 (1H, d, J=8 Hz).

(17) Cyclohexylcarbonyloxymethyl 7-[2-(2-aminothiazol-4-yl)-2-methoxyiminoacetamido]-3-cephem-4-carboxylate (syn isomer).

IR (Nujol): 3410, 3300, 1775, 1745, 1670, 1620 cm$^{-1}$.

NMR (CDCl$_3$, δ): 1.0–2.5 (11H, m), 3.5–3.7 (2H, m), 4.05 (3H, s), 5.08 (1H, d, J=5 Hz), 5.83 (2H, s), 5.92 (2H, s), 6.10 (1H, ABq, J=9.0 Hz, 5.0 Hz), 6.6–6.9 (1H, m), 6.75 (1H, s), 8.00 (1H, d, J=9.0 Hz).

(18) Carboxymethyl 7-[2-(2-aminothiazol-4-yl)-2-methoxyiminoacetamido]-3-cephem-4-carboxylate (syn isomer).

IR (Nujol): 3600, 3410, 3260, 1770, 1720, 1660 cm$^{-1}$.

NMR (DMSO-d$_6$, δ): 3.5–3.8 (2H, broad d), 3.85 (3H, s), 4.73 (2H, s), 5.15 (1H, d, J=8 Hz), 5.87 (1H, q, J=8 Hz, 5 Hz), 6.55–6.87 (2H, m), 6.75 (1H, s), 7.2 (2H, broad s), 9.60 (1H, d, J=8 Hz).

EXAMPLE 20

To a stirred solution of 2,3-di-n-octyloxypropyl iodide (529 mg) in dimethylsulfoxide (14 ml) was added 7-[2-(2-aminothiazol-4-yl)-2-methoxyiminoacetamido]-3-cephem-4-carboxylic acid (syn isomer, 1427 mg) and triethylamine (0.52 ml) at room temperature, and stirred at 40° C. for 4 hours and at 50° C. for 4 hours. The resultant mixture was poured into ice water (200 ml), adjusted to pH 8 with an aqueous solution of sodium bicarbonate and extracted with ethyl acetate (140 ml). The extract was washed with a saturated aqueous solution of sodium chloride (50 ml) and dried over anhydrous magnesium sulfate. The solvent was evaporated under reduced pressure. After washing the residue with n-hexane (8 ml), the residue was triturated with petroleum ether and then the precipitates were collected by filtration to give 2,3-di-n-octyloxypropyl 7-[2-(2-aminothiazol-4-yl)-2-methoxyiminoacetamido]-3-cephem-4-carboxylate (syn isomer, 160 mg), mp. 75° to 78° C.

IR (Nujol): 3400 (shoulder), 3300, 3200 (shoulder), 1780, 1730, 1670 cm$^{-1}$.

NMR (CDCl$_3$, δ): 0.6–2.0 (30H, m), 3.2–3.8 (9H, m), 4.0 (3H, s), 4.1–4.5 (2H, m), 5.03 (1H, d, J=6 Hz), 5.4–6.2 (3H, m), 6.4–6.65 (1H, m), 6.72 (1H, s), 7.8–8.0 (1H, m).

To a cold solution of the above compound in ethyl acetate, was added dropwise hydrochloric acid with stirring, and then the precipitates were collected by filtration to give 2,3-di-n-octyloxypropyl 7-[2-(2-aminothiazol-4-yl)-2-methoxyiminoacetamido]-3-cephem-4-carboxylate hydrochloride (syn isomer).

mp 109°–114° C.

IR (Nujol): 3250, 3150, 1780, 1730, 1665, 1630 cm$^{-1}$.

EXAMPLE 21

Dicyclohexylcarbodiimide (9.0 g) was added to a stirred solution of 7-[2-(2-formamidothiazol-4-yl)-2-methoxyiminoacetamido]-3-cephem-4-carboxylic acid (syn isomer, 10.5 g) and 2-ethoxy-1-ethoxymethylethanol [3.8 g] in a mixture of dried pyridine (120 ml) and dried tetrahydrofuran (37 ml) at 3° C. The reaction mixture was stirred at 0° to 5° C. for 4 hours and then allowed to stand at the same temperature overnight.

The resultant mixture was poured into ice water (500 ml) and extracted with ethyl acetate (450 ml). Ice water (70 ml) was added to the extract, and then the solution was adjusted to pH 2 to 3 with 20% sulfuric acid. The organic layer was separated and washed with a saturated aqueous solution of sodium chloride (200 ml) and an aqueous solution of sodium bicarbonate in turn. The solution was dried over anhydrous magnesium sulfate. The solvent was evaporated under reduced pressure. The residue was subjected to column chromatography on silica gel with a mixture of chloroform and acetone (3:1). The eluate was concentrated under reduced pressure to give 2-ethoxy-1-ethoxymethylethyl 7-[2-(2-formamidothiazol-4-yl)-2-methoxyiminoacetamido]-3-cephem-4-carboxylate (syn isomer, 4.37 g), mp. 104° to 106° C.

IR (Nujol): 3500, 3250, 3200 (shoulder), 1780, 1730, 1680 cm$^{-1}$.

NMR (CDCl$_3$, δ): 1.16 (6H, t, J=7 Hz), 3.3–3.8 (10H, m), 3.93 (3H, s), 4.95–5.35 (2H, m), 6.0 (1H, q, J=8 Hz, 5 Hz), 6.55 (1H, m), 7.23 (1H, s), 7.87 (1H, d, J=8 Hz), 8.5 (1H, s).

EXAMPLE 22

The following compounds were obtained according to similar manners to those of Examples 20 and 21.

(1) 2-Isopropoxy-1-isopropoxymethylethyl 7-[2-(2-formamidothiazol-4-yl)-2-methoxyiminoacetamido]-2-cephem-4-carboxylate (syn isomer).

IR (Nujol): 3500, 3250, 1775, 1745 (shoulder), 1680 cm$^{-1}$.

NMR (CDCl$_3$, δ): 1.15 (12H, d, J=6 Hz), 3.33–3.80 (6H, m), 3.95 (3H, s), 4.9–5.4 (3H, m), 5.7–6.5 (3H, m), 7.18 (1H, s), 7.95 (1H, d, J=9 Hz), 8.53 (1H, s), 11.8 (1H, broad s).

(2) 2-tert-Butoxy-1-tert-butoxymethylethyl 7-[2-(2-formamidothiazol-4-yl)-2-methoxyiminoacetamido]-2-cephem-4-carboxylate (syn isomer).

IR (Nujol): 3500, 3300, 3250, 1775, 1750 (shoulder), 1680 cm$^{-1}$.

NMR (CDCl$_3$, δ): 1.2 (18H, s), 3.55 (4H, d, J=5 Hz), 4.05 (3H, s), 4.9–5.3 (2H, m), 5.35 (1H, d, J=4 Hz), 5.8–6.1 (2H, m), 6.3–6.6 (1H, m), 7.3 (1H, s), 8.0 (1H, d, J=9 Hz), 8.7 (1H, s), 11.8 (1H, broad s).

(3) 2-Isopropoxy-1-isopropoxymethylethyl 7-[2-(2-formamidothiazol-4-yl)-2-methoxyiminoacetamido]-3-cephem-4-carboxylate (syn isomer).

IR (Nujol): 3500, 3220, 1785, 1725, 1680, 1660 cm$^{-1}$.

(4) 2-tert-Butoxy-1-tert-butoxymethylethyl 7-[2-(2-formamidothiazol-4-yl)-2-methoxyiminoacetamido]-3-cephem-4-carboxylate (syn isomer).

IR (Nujol): 3300, 1780, 1720, 1690, 1660 cm$^{-1}$.

(5) 2-Ethoxy-1-ethoxymethylethyl 7-[2-(2-aminothiazol-4-yl)-2-methoxyiminoacetamido]-3-cephem-4-carboxylate (syn isomer).

IR (Nujol): 3400, 3300, 3200 (shoulder), 1775, 1725, 1675 cm$^{-1}$.

(6) 2-Isopropoxy-1-isopropoxymethylethyl 7-[2-(2-aminothiazol-4-yl)-2-methoxyiminoacetamido]-3-cephem-4-carboxylate (syn isomer)

IR (Nujol): 3400, 3300, 3200, 1775, 1725, 1670 cm$^{-1}$.

To a cold solution of the above compound in ethyl acetate, was added dropwise hydrochloric acid with stirring, and then the precipitates were collected by filtration to give 2-isopropoxy-1-isopropoxymethylethyl 7-[2-(2-aminothiazol-4-yl)-2-methoxyiminoacetamido]-3-cephem-4-carboxylate hydrochloride (syn isomer).

mp 120°–125° C.

IR (Nujol): 3250, 3170, 2730, 1785, 1730, 1675, 1630 cm$^{-1}$.

NMR (CDCl₃, δ): 1.15 (12H, d, J=6 Hz), 3.3–4.0 (8H, m), 4.16 (3H, s), 5.0–6.2 (3H, m), 6.5–6.8 (1H, m), 7.20 (1H, s), 8.55 (1H, d, J=9 Hz).

(7) 2-tert-Butoxy-1-tert-butoxymethylethyl 7-[2-(2-aminothiazol-4-yl)-2-methoxyiminoacetamido]-3-cephem-4-carboxylate (syn isomer).

IR (Nujol): 3400, 3300, 3200, 1775, 1725, 1670 cm⁻¹.

EXAMPLE 23

A solution of m-chloroperbenzoic acid (70% purity: 3.2 g) in methylene chloride (50 ml) was dropwise added to a stirred solution of 2-isopropoxy-1-isopropoxymethylethyl 7-[2-(2-formamidothiazol-4-yl)-2-methoxyiminoacetamido]-2-cephem-4-carboxylate (syn isomer, 7.5 g) in methylene chloride (75 ml) at 2° to 5° C. over 25 minutes, and stirred at 0° to 5° C. for 20 minutes. Dimethylsulfide (1 ml) was added to the resultant mixture. The resultant mixture was washed with an aqueous solution of sodium bicarbonate, and a saturated aqueous solution of sodium chloride in turn. After drying the solution over anhydrous magnesium sulfate, the solvent was evaporated under reduced pressure. The residue was triturated with diethylether (100 ml), and then the precipitates were collected by filtration to give 2-isopropoxy-1-isopropoxymethylethyl 7-[2-(2-formamidothiazol-4-yl)-2-methoxyiminoacetamido]-3-cephem-4-carboxylate-1-oxide (syn isomer, 6.77 g).

IR (Nujol): 3500, 3220, 3150 (shoulder), 1790, 1725, 1680 (shoulder), 1660 cm⁻¹.

NMR (CDCl₃, δ): 1.13 (12H, d, J=6 Hz), 3.33–3.83 (8H, m), 3.93 (3H, s), 4.7 (1H, d, J=5 Hz), 5.2 (1H, m), 6.05–6.50 (2H, m), 7.25 (1H, s), 8.30 (1H, d, J=9 Hz), 8.50 (1H, s), 11.6 (1H, broad s).

EXAMPLE 24

The following compound was obtained according to a similar manner to that of Example 23.

(1) 2-tert-Butoxy-1-tert-butoxymethylethyl 7-[2-(2-formamidothiazol-4-yl)-2-methoxyiminoacetamido]-3-cephem-4-carboxylate-1-oxide (syn isomer).

IR (Nujol): 3500, 3320, 3240, 1790, 1720, 1690 (shoulder), 1660 cm⁻¹.

NMR (CDCl₃, δ): 1.2 (18H, s), 3.4–3.7 (6H, m), 3.9 (3H, s), 4.75 (1H, d, J=4 Hz), 5.1 (1H, m), 6.2 (1H, q, J=8 Hz, 4 Hz), 6.35 (1H, m), 7.3 (1H, s), 8.35 (1H, d, J=8 Hz), 8.5 (1H, s).

EXAMPLE 25

To a stirred solution of 2-isopropoxy-1-isopropoxymethylethyl 7-[2-(2-formamidothiazol-4-yl)-2-methoxyiminoacetamido]-3-cephem-4-carboxylate-1-oxide (syn isomer, 6.5 g) and sodium iodide (5 g) in dried acetone (130 ml) was dropwise added trifluoroacetic anhydride (7 g) at −2° C. over 16 minutes, and stirred at 0° to 5° C. for 1.2 hours. The resultant mixture was poured into ice water (650 ml), and then extracted with ethyl acetate (200 ml). The extract was washed with an aqueous solution of sodium sulfite (50 ml) and a saturated aqueous solution of sodium chloride (50 ml) in turn. The solution was dried over anhydrous magnesium sulfate. The solvent was evaporated under reduced pressure and the residue was triturated with diethylether (100 ml). The precipitates were collected by filtration to give 2-isopropoxy-1-isopropoxymethylethyl 7-[2-(2-formamidothiazol-4-yl)-2-methoxyiminoacetamido]-3-cephem-4-carboxylate (syn isomer, 5.6 g).

IR (Nujol): 3500, 3220, 1785, 1725, 1680, 1660 cm⁻¹.

NMR (CDCl₃, δ): 1.13 (12H, d, J=6 Hz), 3.40–3.85 (8H, m), 3.97 (3H, s), 5.03–5.37 (2H, m), 5.8–6.2 (1H, m), 6.6 (1H, m), 7.23 (1H, s), 7.92 (1H, d, J=8 Hz), 8.57 (1H, s).

EXAMPLE 26

The following compound was obtained according to a similar manner to that of Example 25.

(1) 2-tert-Butoxy-1-tert-butoxymethylethyl 7-[2-(2-formamidothiazol-4-yl)-2-methoxyiminoacetamido]-3-cephem-4-carboxylate (syn isomer).

IR (Nujol): 3300, 1780, 1720, 1690, 1660 cm⁻¹.

NMR (CDCl₃, δ): 1.2 (18H, s), 3.4–3.8 (6H, m), 4.0 (3H, s), 5.0–5.3 (2H, m), 5.95–6.2 (1H, m), 6.65 (1H, m), 7.25 (1H, s), 8.0 (1H, d, J=9 Hz), 8.6 (1H, s), 11.8 (1H, broad s).

EXAMPLE 27

To a stirred solution of 2-ethoxy-1-ethoxymethylethyl 7-[2-(2-formamidothiazol-4-yl)-2-methoxyiminoacetamido]-3-cephem-4-carboxylate (syn isomer, 2.85 g) in methanol (57 ml) was slowly added conc. hydrochloric acid (1.13 ml) at room temperature, and stirred at room temperature for 3 hours. The resultant mixture was poured into ice water (280 ml), adjusted to pH 7 to 8 with an aqueous solution of sodium bicarbonate, and then extracted with ethyl acetate (150 ml). The extract was washed with a saturated aqueous solution of sodium chloride and dried over anhydrous magnesium sulfate. After the solvent was evaporated under reduced pressure, the residue was subjected to column chromatography on silica gel with a mixture of chloroform and methaol (30:1). The eluate was concentrated under reduced pressure to give 2-ethoxy-1-ethoxymethylethyl 7-[2-(2-aminothiazol-4-yl]-2-methoxyiminoacetamido]-3-cephem-4-carboxylate (syn isomer, 1.77 g), mp. 95° to 97° C.

IR (Nujol): 3400, 3300, 3200 (shoulder), 1775, 1725, 1675 cm⁻¹.

NMR (CDCl₃, δ): 1.17 (6H, t, J=7 Hz), 3.3–3.7 (10H, m), 4.0 (3H, s), 4.9–5.4 (2H, m), 5.65–6.15 (3H, m), 6.5 (1H, m), 6.7 (1H, s), 7.92 (1H, d, J=9 Hz).

EXAMPLE 28

The following compounds were obtained according to a similar manner to that of Example 27.

(1) 2-Isopropoxy-1-isopropoxymethylethyl 7-[2-(2-aminothiazol-4-yl)-2-methoxyiminoacetamido]-3-cephem-4-carboxylate (syn isomer), mp. 102° to 106° C.

IR (Nujol): 3400, 3300, 3200, 1775, 1725, 1670 cm⁻¹.

NMR (CDCl₃, δ): 1.13 (12H, d, J=6 Hz), 3.37–3.83 (8H, m), 4.0 (3H, s), 4.97–5.40 (2H, m), 5.73 (2H, broad s), 6.02 (1H, q, J=9 Hz, 5 Hz), 6.55 (1H, m), 6.73 (1H, s), 7.83 (1H, d, J=9 Hz).

(2) 2-tert-Butoxy-1-tert-butoxymethylethyl 7-[2-(2-aminothiazol-4-yl)-2-methoxyiminoacetamido]-3-cephem-4-carboxylate (syn isomer), mp 120.5° to 124.5° C.

IR (Nujol): 3400, 3300, 3200, 1775, 1725, 1670 cm⁻¹.

NMR (CDCl₃, δ): 1.15 (18H, s), 3.4–3.7 (6H, m), 4.05 (3H, s), 5.05 (1H, d, J=5 Hz), 4.9–5.2 (1H, m), 5.7 (2H, broad s), 6.0 (1H, q, J=9 Hz, 5 Hz), 6.5 (1H, m), 6.7 (1H, s), 7.8 (1H, d, J=9 Hz).

EXAMPLE 29

| Compound A | 50 mg |
|---|---|
| Ethyl cellulose | 10 mg |
| Migryol 812 | 1 ml |

Compound A [i.e. 2-n-butoxy-1-n-butoxymethylethyl 7-[2-(2-aminothiazol-4-yl]-2-methoxyiminoacetamido]-3-cephem-4-carboxylate (syn isomer) was suspended in Migryol 812 [Trademark: Manufactured by Dynamit Nobel Chemicals] and ethyl cellulose to produce the composition for oral administration.

The following compounds were used instead of the compound A [i.e. 2-n-butoxy-1-n-butoxymethylethyl 7-[2-(2-aminothiazol-4-yl)-2-methoxyiminoacetamido]-3-cephem-4-carboxylate (syn isomer)].

(1) n-Hexyl 7-[2-(2-aminothiazol-4-yl)-2-methoxyiminoacetamido]-3-cephem-4-carboxylate (syn isomer).

(2) n-Octyl 7-[2-(2-aminothiazol-4-yl)-2-methoxyiminoacetamido]-3-cephem-4-carboxylate (syn isomer).

(3) n-Decyl 7-[2-(2-aminothiazol-4-yl)-2-methoxyiminoacetamido]-3-cephem-4-carboxylate (syn isomer).

(4) 2-Pyridylmethyl 7-[2-(2-aminothiazol-4-yl)-2-methoxyiminoacetamido]-3-cephem-4-carboxylate (syn isomer).

(5) 2-n-Octyloxy-1-n-octyloxymethylethyl 7-[2-(2-aminothiazol-4-yl)-2-methoxyiminoacetamido]-3-cephem-4-carboxylate (syn isomer).

(6) 2-n-Dodecyloxy-1-n-dodecyloxymethylethyl 7-[2-(2-aminothiazol-4-yl)-2-methoxyiminoacetamido]-3-cephem-4-carboxylate (syn isomer).

(7) 2-n-Nonanoyloxy-1-n-nonanoyloxymethylethyl 7-[2-(2-aminothiazol-4-yl)-2-methoxyiminoacetamido]-3-cephem-4-carboxylate (syn isomer).

(8) 4-Nitrobenzyloxycarbonylmethyl 7-[2-(2-aminothiazol-4-yl)-2-methoxyiminoacetamido]-3-cephem-4-carboxylate (syn isomer).

(9) 5-(4-Nitrobenzyloxycarbonyl)pentyl 7-[2-(2-aminothiazol-4-yl)-2-methoxyiminoacetamido]-3-cephem-4-carboxylate (syn isomer).

(10) 3-(4-Nitrobenzyloxycarbonyl)propyl 7-[2-(2-aminothiazol-4-yl)-2-methoxyiminoacetamido]-3-cephem-4-carboxylate (syn isomer).

(11) tert-Butoxycarbonyloxymethyl 7-[2-(2-aminothiazol-4-yl)-2-methoxyiminoacetamido]-3-cephem-4-carboxylate (syn isomer).

(12) 1-Diphenylmethoxycarbonylpropyl 7-[2-(2-aminothiazol-4-yl)-2-methoxyiminoacetamido]-3-cephem-4-carboxylate (syn isomer).

(13) 5-Carboxypentyl 7-[2-(2-aminothiazol-4-yl)-2-methoxyiminoacetamido]-3-cephem-4-carboxylate (syn isomer).

(14) 3-Carboxypropyl 7-[2-(2-aminothiazol-4-yl)-2-methoxyiminoacetamido]-3-cephem-4-carboxylate (syn isomer).

(15) 1-Carboxypropyl 7-[2-(2-aminothiazol-4-yl)-2-methoxyiminoacetamido]-3-cephem-4-carboxylate (syn isomer).

(16) Cyclohexylcarbonyloxymethyl 7-[2-(2-aminothiazol-4-yl)-2-methoxyiminoacetamido]-3-cephem-4-carboxylate (syn isomer).

(17) Carboxymethyl 7-[2-(2-aminothiazol-4-yl)-2-methoxyiminoacetamido]-3-cephem-4-carboxylate (syn isomer).

(18) 2,3-Di-n-octyloxypropyl 7-[2-(2-aminothiazol-4-yl)-2-methoxyiminoacetamido]-3-cephem-4-carboxylate (syn isomer).

(19) 2-Ethoxy-1-ethoxymethylethyl 7-[2-(2-aminothiazol-4-yl)-2-methoxyiminoacetamido]-3-cephem-4-carboxylate (syn isomer).

(20) 2-Isopropoxy-1-isopropoxymethylethyl 7-[2-(2-aminothiazol-4-yl)-2-methoxyiminoacetamido]-3-cephem-4-carboxylate (syn isomer).

(21) 2-tert-Butoxy-1-tert-butoxymethylethyl 7-[2-(2-aminothiazol-4-yl)-2-methoxyiminoacetamido]-3-cephem-4-carboxylate (syn isomer).

EXAMPLE 30

To a solution of sodium 7-[2-(2-aminothiazol-4-yl)-2-methoxyiminoacetamido]-3-cephem-4-carboxylate (syn isomer) (4.0 g) in dimethylsulfoxide (40 ml) was added isopropyl 1-iodoethoxyformate (5.1 g). The mixture was stirred for 30 minutes at ambient temperature and poured into a mixture of cold water and ethyl acetate. The organic layer was separated out and the aqueous layer was extracted with ethyl acetate. The organic layers were combined, washed with water, dried over magnesium sulfate and evaporated to dryness. The residue was subjected to column chromatography on silica gel (50 g) using a mixture of benzene and ethyl acetate (3:2) as an eluent. The eluates containing an object compound were collected and evaporated to dryness to give 1-isopropoxycarbonyloxyethyl 7-[2-(2-aminothiazol-4-yl)-2-methoxyiminoacetamido]-3-cephem-4-carboxylate (syn isomer) (1.5 g), mp 120° to 125° C. (dec.).

IR (Nujol): 3450, 3370, 3150, 1790, 1760, 1680, 1620 cm$^{-1}$.

NMR (DMSO-$d_6$, $\delta$): 1.25 (6H, d, J=6 Hz), 1.50 (3H, d, J=5 Hz), 3.4–3.9 (2H, m), 3.85 (3H, s), 4.5–5.1 (1H, m), 5.13 (1H, d, J=5 Hz), 5.87 (1H, 2d, J=5 Hz, 8 Hz), 6.5–6.8 (2H, m), 6.73 (1H, s), 7.20 (2H, broad s), 9.57 (1H, d, J=8 Hz).

To a cold solution of the above compound in ethyl acetate, was added dropwise hydrochloric acid with stirring, and then the precipitates were collected by filtration to give 1-isopropoxycarbonyloxyethyl 7-[2-(2-aminothiazol-4-yl)-2-methoxyiminoacetamido]-3-cephem-4-carboxylate hydrochloride (syn isomer).

mp 151°–156° C. (dec).

IR (Nujol): 3250, 1790, 1755, 1660, 1630, 1545, 1400, 1290, 1265, 1160, 1100, 1075, 1050 cm$^{-1}$.

NMR (DMSO-$d_6$, $\delta$): 1.25 (6H, d, J=6 Hz), 1.52 (3H, d J=6 Hz), 3.6–3.9 (2H, m), 3.97 (3H, s), 4.5–5.2 (2H, m), 5.20 (1H, d, J=5 Hz), 5.89 (1H, dd, J=5 Hz, 7 Hz), 6.5–7.0 (2H, m), 6.97 (1H, s), 7.4 (3H, broad s), 9.65 (1H, d, J=7 Hz).

EXAMPLE 31

The following compounds were obtained according to a similar manner to that of Example 30.

(1) 1-(2-Azidoethoxycarbonyloxy)ethyl 7-[2-(2-aminothiazol-4-yl)-2-methoxyiminoacetamido]-3-cephem-4-carboxylate (syn isomer), mp 100° to 110° C. (dec.).

IR (Nujol): 3300, 2090, 1780–1760, 1670 cm$^{-1}$.

NMR (DMSO-$d_6$, $\delta$): 1.53 (3H, d, J=5 Hz), 3.6 (4H, m), 3.85 (3H, s), 4.30 (2H, t, J=4 Hz), 5.15 (1H, d, J=5 Hz), 5.86 (1H, dd, J=5 Hz, 8 Hz), 6.7 (2H, m), 6.75 (1H, s), 7.18 (2H, s), 9.60 (1H, d, J=8 Hz).

(2) 1-Benzoyloxyethyl 7-[2-(2-aminothiazol-4-yl)-2-methoxyiminoacetamido]-3-cephem-4-carboxylate (syn isomer), mp 140° to 150° C. (dec.).
IR (Nujol): 3300, 1773, 1734, 1670 cm$^{-1}$.
NMR (DMSO-$d_6$, $\delta$): 1.70 (3H, d, J=5 Hz), 3.6 (2H, m), 3.88 (3H, s), 5.20 (1H, d, J=5 Hz), 5.7–6.2 (1H, m), 6.67 (1H, m), 6.76 (1H, s), 7.2 (3H, m), 7.4–8.1 (5H, m).
(3) 1-Ethoxycarbonyloxyethyl 7-[2-(2-aminothiazol-4-yl)-2-methoxyiminoacetamido]-3-cephem-4-carboxylate (syn isomer), mp 120° to 130° C. (dec.).
IR (Nujol): 3310, 1780–1755, 1670 cm$^{-1}$.
NMR (DMSO-$d_6$, $\delta$): 1.25 (3H, t, J=8 Hz), 1.51 (3H, d, J=5.5 Hz), 3.63 (2H, m), 3.83 (3H, s), 4.02 (2H, q, J=8 Hz), 5.12 (1H, d, J=4.5 Hz), 5.85 (1H, dd, J=4.5 Hz, 8 Hz), 6.60 (1H, t, J=3.5 Hz), 6.71 (1H, s), 6.80 (1H, q, J=5.5 Hz), 7.15 (2H, s), 9.53 (1H, d, J=8 Hz).
(4) 3-Phthalidyl 7-[2-(2-aminothiazol-4-yl)-2-methoxyiminoacetamido]-3-cephem-4-carboxylate (syn isomer), mp 200° to 205° C. (dec.).
IR (Nujol): 3310, 1780, 1744, 1670 cm$^{-1}$.
NMR (DMSO-$d_6$, $\delta$): 3.6 (2H, m), 3.83 (3H, s), 5.12 (1H, d, J=4.5 Hz), 5.80 (1H, dd, J=4.5 Hz, 7.5 Hz), 6.65 (1H, m), 6.68 (1H, s), 7.56, 7.66 (1H, s), 7.80 (4H, s), 9.52 (1H, d, J=7.5 Hz).
(5) Tetradecanoyloxymethyl 7-[2-(2-aminothiazol-4-yl)-2-methoxyiminoacetamido]-3-cephem-4-carboxylate (syn isomer), mp 133° to 137° C. (dec.).
IR (Nujol): 3420, 3310, 1770, 1750, 1730, 1670, 1620, 1530, 1280, 1210 cm$^{-1}$.
NMR (DMSO-$d_6$, $\delta$): 0.86 (3H, t, J=5 Hz), 1.26 (20H, s), 1.4–1.7 (2H, m), 2.36 (2H, t, J=6 Hz), 3.6 (2H, m), 3.86 (3H, s), 5.12 (1H, d, J=5 Hz), 5.6–6.0 (3H, m), 6.5–6.7 (1H, m), 6.72 (1H, s), 7.18 (2H, broad s), 9.54 (1H, d, J=9 Hz).
(6) 2,3-Dimethylpentanoyloxymethyl 7-[2-(2-aminothiazol-4-yl)-2-methoxyiminoacetamido]-3-cephem-4-carboxylate (syn isomer).
IR (Nujol): 3400, 3300, 1770, 1745, 1670, 1620 cm$^{-1}$.
NMR (CDCl$_3$, $\delta$): 0.9–2.0 (13H, m), 3.5–3.7 (2H, m), 4.00 (3H, s), 5.03 (1H, d, J=5 Hz), 5.87 (2H, s), 6.0 (2H, s), 6.03 (1H, ABq, J=5 Hz, 9 Hz), 6.6–6.8 (1H, m), 6.67 (1H, s), 8.07 (1H, d, J=9 Hz).
To a cold solution of the above compound in ethyl acetate, was added dropwise hydrochloric acid with stirring, and then the precipitates were collected by filtration to give 2,3-dimethylpentanoyloxymethyl 7-[2-(2-aminothiazol-4-yl)-2-methoxyiminoacetamido]-3-cephem-4-carboxylate hydrochloride (syn isomer).
mp 119°–122° C.
IR (Nujol): 3250, 3150, 2730, 1785, 1755, 1675, 1630 cm$^{-1}$.
NMR (CDCl$_3$, $\delta$): 0.6–2.1 (11H, m), 2.2–2.7 (1H, m), 3.4–3.9 (2H, m), 4.13 (3H, s), 5.12 (1H, d, J=5 Hz), 5.3–6.3 (4H, m), 6.5–6.8 (1H, m), 7.15 (1H, s), 8.67 (1H, d, J=8 Hz).

EXAMPLE 31-(7)

To a solution of sodium 7-[2-(2-aminothiazol-4-yl)-2-methoxyiminoacetamido]-3-cephem-4-carboxylate (syn isomer, 2.02 g) in dimethylsulfoxide (35 ml) was added ethyl 1-iodoethyl carbonate (4 g) and the mixture was stirred for 10 minutes at ambient temperature. The reaction mixture was poured into a mixture of cold water (150 ml) and ethyl acetate, and the organic layer was separated out. The aqueous layer was extracted with ethyl acetate and the combined extracts were washed with 5% aqueous sodium thiosulfate and an aqueous sodium chloride, followed by drying over magnesium sulfate. The solution was concentrated to 50 ml under reduced pressure and subjected to column chromatography on silica gel (50 g) using a mixed solvent of benzene and ethyl acetate (3:2 to 2:3) as an eluent. The eluates containing an object compound were collected and evaporated to dryness to give amorphous precipitates of 1-ethoxycarbonyloxyethyl 7-[2-(2-aminothiazol-4-yl)-2-methoxyiminoacetamido]-3-cephem-4-carboxylate (syn isomer, (0.9 g), mp 120° to 130° C. (dec.).

EXAMPLE 32

To a solution of sodium 7-[2-(2-aminothiazol-4-yl)-2-methoxyiminoacetamido]-3-cephem-4-carboxylate (syn isomer) (1.4 g) in N,N-dimethylformamide (40 ml) was added 3-phthalidylideneethyl bromide (1.0 g), and the mixture was stirred at ambient temperature for 15 minutes. The reaction mixture was poured into a mixture of water and ethyl acetate (each 200 ml) with stirring. The separated organic solution was washed with 5% aqueous sodium bicarbonate and then water, followed by drying over magnesium sulfate. The resultant solution was evaporated to dryness to give 2-(3-phthalidylidene)ethyl 7-[2-(2-aminothiazol-4-yl)-2-methoxyiminoacetamido]-3-cephem-4-carboxylate (syn isomer) (1.5 g), mp 150° to 156° C. (dec.).
IR(Nujol): 3300, 1780, 1725, 1680, 1620 cm$^{-1}$.
NMR(DMSO-$d_6$, $\delta$): 3.65(2H,q,J=17 Hz), 3.83(3H,s), 5.12(1H,d,J=5 Hz), 5.16(2H,d,J=7 Hz), 5.95(1H,dd,J=5 Hz, 8 Hz), 6.17(1H, t,J=7 Hz), 6.62(1H,m), 6.75(1H,s), 7.63–8.25(4H,m), 9.60(1H,d,J=8 Hz).

EXAMPLE 33

2-n-Dodecyloxy-1-n-dodecyloxymethyl 7-[2-(2-aminothiazol-4-yl)-2-methoxyiminoacetamido]-2-cephem-4-carboxylate (syn isomer) was prepared by reacting 7-[2-aminothiazol-4-yl)-2-methoxyiminoacetamido]-3-cephem-4-carboxylic acid (syn isomer) with 2-n-dodecyloxy-1-n-dodecyloxymethylethanol in the presence of benzenesulfonyl chloride according to a similar manner to that of Example 7.
IR (Nujol): 3250, 1795, 1735, 1695, 1670 cm$^{-1}$.

EXAMPLE 34

The following compounds were obtained according to the similar manner to those of Examples 17 and 18.
(1) 1-Isopropoxycarbonyloxyethyl 7-[2-(2-aminothiazol-4-yl)-2-methoxyiminoacetamido]-3-cephem-4-carboxylate (syn isomer).
IR (Nujol): 3450, 3370, 3150, 1790, 1760, 1680 cm$^{-1}$.
To a cold solution of the above compound in ethyl acetate, was added dropwise hydrochloric acid with stirring, and then the precipitates were collected by filtration to give 1-isopropoxycarbonyloxyethyl 7-[2-(2-aminothiazol-4-yl)-2-methoxyiminoacetamido]-3-cephem-4-carboxylate hydrochloride (syn isomer).
mp 151°–156° C. (dec).
IR (Nujol): 3250, 1790, 1755, 1660, 1630, 1545, 1400, 1290, 1265, 1160, 1100, 1075, 1050 cm$^{-1}$.
NMR (DMSO-$d_6$, $\delta$): 1.25 (6H, d, J=6 Hz), 1.52 (3H, d, J=6 Hz), 3.6–3.9 (2H, m), 3.97 (3H, s), 4.5–5.2 (2H, m), 5.20 (1H, d, J=5 Hz), 5.89 (1H, dd, J=5 Hz, 7 Hz), 6.5–7.0 (2H, m), 6.97 (1H, s), 7.4 (3H, broad s), 9.65 (1H, d, J=7 Hz).
(2) 1-(2-Azidoethoxycarbonyloxy)ethyl 7-[2-(2-aminothiazol-4-yl)-2-methoxyiminoacetamido]-3-cephem-4-carboxylate (syn isomer), mp 100° to 110° C. (dec.).
IR (Nujol): 3300, 2090, 1780–1760, 1670 cm$^{-1}$.

NMR (DMSO-d$_6$, δ): 1.53 (3H, d, J=5 Hz), 3.6 (4H, m), 3.85 (3H, s), 4.30 (2H, t, J=4 Hz), 5.15 (1H, d, J=5 Hz), 5.86 (1H, dd, J=5 Hz, 8 Hz), 6.7 (2H, m), 6.75 (1H, s), 7.18 (2H, s), 9.60 (1H, d, J=8 Hz).

(3) 1-Benzoyloxyethyl 7-[2-(2-aminothiazol-4-yl)-2-methoxyiminoacetamido]-3-cephem-4-carboxylate (syn isomer), mp 140° to 150° C. (dec.).

IR (Nujol): 3300, 1773, 1734, 1670 cm$^{-1}$.

NMR (DMSO-d$_6$, δ): 1.70 (3H, d, J=5 Hz), 3.6 (2H, m), 3.88 (3H, s), 5.20 (1H, d, J=5 Hz), 5.7-6.2 (1H, m), 6.67 (1H, m), 6.76 (1H, s), 7.2 (3H, m), 7.4-8.1 (5H, m).

(4) 1-Ethoxycarbonyloxyethyl 7-[2-(2-aminothiazol-4-yl)-2-methoxyiminoacetamido]-3-cephem-4-carboxylate (syn isomer), mp 120° to 130° C. (dec.).

IR (Nujol): 3310, 1780-1755, 1670 cm$^{-1}$.

NMR (DMSO-d$_6$, δ): 1.23 (3H, t, J=8 Hz), 1.51 (3H, d, J=5.5 Hz), 3.63 (2H, m), 3.83 (3H, s), 4.02 (2H, q, J=8 Hz), 5.12 (1H, d, J=4.5 Hz), 5.85 (1H, dd, J=4.5 Hz, 8 Hz), 6.60 (1H, t, J=3.5 Hz), 6.71 (1H, s), 6.80 (1H, q, J=5.5 Hz), 7.15 (2H, s), 9.53 (1H, d, J=8 Hz).

(5) 3-Phthalidyl 7-[2-(2-aminothiazol-4-yl)-2-methoxyiminoacetamido]-3-cephem-4-carboxylate (syn isomer), mp 200° to 205° C. (dec.).

IR (Nujol): 3310, 1780, 1744, 1670 cm$^{-1}$.

NMR (DMSO-d$_6$, δ): 3.6 (2H, m), 3.83 (3H, s), 5.12 (1H, d, J=4.5 Hz), 5.80 (1H, dd, J=4.5 Hz, 7.5 Hz), 6.65 (1H, m), 6.68 (1H, s), 7.56, 7.66 (1H, s), 7.80 (4H, s), 9.52 (1H, d, J=7.5 Hz).

(6) Tetradecanoyloxymethyl 7-[2-(2-aminothiazol-4-yl)-2-methoxyiminoacetamido]-3-cephem-4-carboxylate (syn isomer), mp 133° to 137° C. (dec.).

IR (Nujol): 3420, 3310, 1770, 1750, 1730, 1670, 1620, 1530, 1280, 1210 cm$^{-1}$.

NMR (DMSO-d$_6$, δ): 0.86 (3H, t, J=5 Hz), 1.26 (20H, s), 1.4-1.7 (2H, m), 2.36 (2H, t, J=6 Hz), 3.6 (2H, m), 3.86 (3H, s), 5.12 (1H, d, J=5 Hz), 5.6-6.0 (3H, m), 6.5-6.7 (1H, m), 6.72 (1H, s), 7.18 (2H, broad s), 9.54 (1H, d, J=9 Hz).

(7) 2,3-Dimethylpentanoyloxymethyl 7-[2-(2-aminothiazol-4-yl)-2-methoxyiminoacetamido]-3-cephem-4-carboxylate (syn isomer).

IR (Nujol): 3400, 3300, 1770, 1745, 1670, 1620 cm$^{-1}$.

NMR (CDCl$_3$, δ): 0.9-2.0 (13H, m), 3.5-3.7 (2H, m), 4.00 (3H, s), 5.03 (1H, d, J=5 Hz), 5.87 (2H, s), 6.0 (2H, s), 6.03 (1H, ABq, J=5 Hz, 9 Hz), 6.6-6.8 (1H, m), 6.67 (1H, s), 8.07 (1H, d, J=9 Hz).

(8) 2-(3-Phthalidylideneethyl 7-[2-(2-aminothiazol-4-yl)-2-methoxyiminoacetamido]-3-cephem-4-carboxylate (syn isomer).

IR (Nujol): 3300, 1780, 1725, 1680, 1620 cm$^{-1}$.

EXAMPLE 35

The following compounds were used instead of the compound A in Example 29.

(1) 1-Isopropoxycarbonyloxyethyl 7-[2-(2-aminothiazol-4-yl)-2-methoxyiminoacetamido]-3-cephem-4-carboxylate (syn isomer).

(2) 1-(2-Azidoethoxycarbonyloxy)ethyl 7-[2-(2-aminothiazol-4-yl)-2-methoxyiminoacetamido]-3-cephem-4-carboxylate (syn isomer).

(3) 1-Benzoyloxyethyl 7-[2-(2-aminothiazol-4-yl)-2-methoxyiminoacetamido]-3-cephem-4-carboxylate (syn isomer).

(4) 1-Ethoxycarbonyloxyethyl 7-[2-(2-aminothiazol-4-yl)-2-methoxyiminoacetamido]-3-cephem-4-carboxylate (syn isomer).

(5) 3-Phthalidyl 7-[2-(2-aminothiazol-4-yl)-2-methoxyiminoacetamido]-3-cephem-4-carboxylate (syn isomer).

(6) Tetradecanoyloxymethyl 7-[2-(2-aminothiazol-4-yl)-2-methoxyiminoacetamido]-3-cephem-4-carboxylate (syn isomer).

(7) 2,3-Dimethylpentanoyloxymethyl 7-[2-(2-aminothiazol-4-yl)-2-methoxyiminoacetamido]-3-cephem-4-carboxylate (syn isomer).

(8) 2-(3-Phthalidylidene)ethyl 7-[2-(2-aminothiazol-4-yl)-2-methoxyiminoacetamido]-3-cephem-4-carboxylate (syn isomer).

What we claim is:

1. Tert-butoxycarbonylmethyl 7-[2-(2-aminothiazol-4-yl)-2-methoxyiminoacetamido]-3-cephem-4-carboxylate (syn isomer).

2. An antimicrobial pharmaceutical composition comprising, as an active ingredient, an effective amount of the compound claimed in claim 1 in admixture with pharmaceutically acceptable carriers.

3. A method for treating infectious diseases caused by pathogenic microorganisms, which comprises administering an effective amount of the compound claimed in claim 1 to infected human being or animals.

* * * * *